(12) United States Patent
Aoyagi et al.

(10) Patent No.: US 7,776,542 B1
(45) Date of Patent: Aug. 17, 2010

(54) METHODS FOR THE DETECTION OF HEPATITIS B AND C VIRUSES

(75) Inventors: Katsumi Aoyagi, Saitama (JP); Chiharu Ohue, Saitama (JP); Kumiko Iida, Saitama (JP); Tatsuji Kimura, Saitama (JP); Shintaro Yagi, Saitama (JP)

(73) Assignee: Advanced Life Science Institute (JP)

( * ) Notice: Subject to any disclaimer, the term of this patent is extended or adjusted under 35 U.S.C. 154(b) by 0 days.

(21) Appl. No.: 09/269,897

(22) PCT Filed: Aug. 4, 1998

(86) PCT No.: PCT/JP98/03476
§ 371 (c)(1),
(2), (4) Date: Apr. 2, 1999

(87) PCT Pub. No.: WO99/06836
PCT Pub. Date: Feb. 11, 1999

(30) Foreign Application Priority Data

| Aug. 4, 1997 | (JP) | ................................. | 9-209515 |
| Aug. 4, 1997 | (JP) | ................................. | 9-209522 |
| Jul. 31, 1998 | (JP) | ................................. | 10-218136 |

(51) Int. Cl.
G01N 33/53 (2006.01)
G01N 33/569 (2006.01)
G01N 33/576 (2006.01)

(52) U.S. Cl. .............................. 435/7.1; 435/5; 435/7.2

(58) Field of Classification Search ...................... 422/1; 424/405, 487; 435/238, 235.1, 236
See application file for complete search history.

(56) References Cited

U.S. PATENT DOCUMENTS

| 4,148,869 A | | 4/1979 | Deaton |
| 5,081,010 A | * | 1/1992 | Cummins et al. .............. 435/5 |
| 5,124,245 A | | 6/1992 | Cummins et al. |
| 5,136,027 A | | 8/1992 | Pope |
| 5,155,021 A | | 10/1992 | Sutton et al. |
| 5,547,976 A | | 8/1996 | Slater et al. |
| 5,625,034 A | | 4/1997 | Liao et al. |
| 5,633,349 A | | 5/1997 | Reichl |
| 6,074,646 A | * | 6/2000 | Cloyd et al. ............. 424/188.1 |

FOREIGN PATENT DOCUMENTS

| CA | 2002856 | 11/1990 |
| EP | 0161328 | 11/1985 |
| EP | 0 272 483 A1 | 6/1988 |
| EP | 0 337 785 A1 | 4/1989 |
| EP | 0717104 | 6/1996 |
| EP | 0 717 104 A2 | 7/1996 |
| JP | 53-104724 | 9/1978 |
| JP | 60-4938 | 2/1985 |
| JP | 63-185996 | 8/1988 |
| JP | 06300761 | 10/1994 |
| JP | 8-29427 | 2/1996 |
| JP | 8-50133 | 2/1996 |
| WO | WO 87/02250 | 4/1987 |
| WO | WO 92/19285 | * 11/1992 |

OTHER PUBLICATIONS

Orito et al., "Quantification of serum hepatitis C virus core protein level in patients chronically infected with different hepatitis C virus genotypes", *Gut*, 1996; 39; 876-880.

Tanaka et al., "Simple fluorescent enzyme immunoassay for detection and quantification of hepatitis C viremia", *Journal of Hepatology*, 1995; 23; 742-745.

Kashiwakuma et al., "Detection of hepatitis C virus specific core protein in serum of patients by a sensitive fluorescence enzyme immunoassay (FEIA)", *Journal of Immunological Methods*, 1996; 190; 79-89.

Takahashi et al., "Demonstration of a hepatitis C virus-specific antigen predicted from the putative core in the circulation of infected hosts", *Journal of General Virology*, 1992; 73; 667-672.

Tanaka et al., "Serum levels of Hepatitis C Viirus Core Protein in Patients With Chronic Hepatitis C Treated With Interferon Alfa", *Hepatology*, 1996; 23; 1330-1333.

Office Action issued in the Canadian Patent Office for Canadian Patent Application No. 2,267,207 citing the two references listed below.

Virologies, 1989, vol. 40, pp. 189-196, by R. Repanovici, et al.

Proc. Natl. Acad. Sci. U.S.A., 1981, vol. 78, pp. 4606-4610, by S.B. Prusiner, et al.

M.L. Khristova, Antigenic reactivity of matrix protein and nucleoprotein of influenza virus . . . , Opposition against EP Patent 967484 /98 93 5359.4.

John J. Oprandy, Improved enzyme-linked immunosorbent assay . . . , Diagn Microbio Infect Dis, 1987; 7:55-58.

Amphotere Tenside, Wikipedia der frein Enzyklopadie.

Fritz H. Kayser, et al., Medizinische Mikrobiologie, Immunologie, Bakteriologie, Mykologie, Virologie, Parasitologie.

(Continued)

Primary Examiner—Robert A Zeman
(74) Attorney, Agent, or Firm—Baker & Hostetler, LLP

(57) ABSTRACT

A method for treating a virus-containing sample, characterized by treatment of a virus-containing sample with a treatment solution containing (1) an anionic surfactant and (2) an amphoteric surfactant, nonionic surfactant or protein denaturant; a virus assay method using said treating method; a method for treating a virus-containing sample, characterized by treatment of a virus-containing sample with a treatment solution containing (1) a chaotropic ion and (2) an acidifying agent; a virus assay method using said treating method; a virus assay method, characterized in that a virus antigen and a virus antibody are measured based on their binding to their probe in the presence of a surfactant with an alkyl group of 10 or more carbon atoms and a secondary, tertiary or quaternary amine, or a nonionic surfactant, or of both of them; and a monoclonal antibody and a hybridoma producing the same for carrying out said method.

12 Claims, 17 Drawing Sheets

OTHER PUBLICATIONS

Ralf Bartenschlager, et al., Complex Formation between the NS3 serine-type proteinase . . . , Journal of Virology, Dec. 1995, p. 7519-7528.

Tomiko Kashiwakuma, et al., Detection of hepatitis C virus specific core protein in serum of patients . . . , Journal of Immunological 190 '96 79-89.

Katsumi Aoyagi, et al., Development of a Simple and highly sensitive enzyme immunoassay for Hepatitis C . . . , Journal of Clinical Microbiology, Jun. 1999, 1802-1808.

EP 1 801 591 A2, Artificial Sequence, Opposition against EP Patent 967484.

Vossius & Partner, 80298 Munich.

Application No. 98935359.4—2004 / 0967484, Communication of notice of opposition.

Journal Of Immunological Methods 190 (1996), pp. 79-89, "Detection Of Hepatitis C Virus Specific Core Protein In Serum Of Patients By A Sensitive Fluorescence Enzyme Immunoassay (FEIA)" by Kashiwakuma, et al.

Partial Search Report of the corresponding European Patent Application, and copies of the above-cited references.

* cited by examiner

METHODS FOR THE DETECTION OF HEPATITIS B AND C VIRUSES

The Sequence Listing associated with this application is filed in electronic format via EFS-Web and hereby incorporated by reference into the specification in its entirety. The name of the text file containing the Sequence Listing is 09269897Sequence.txt, and it lists SEQ ID NOs 1-8 as described in the present patent application. This file was created on Jul. 10, 2009 and has a file size of 4,547 bytes. The sequences listed the file 09269897Sequence.txt are the same as those originally submitted to the United States Patent and Trademark Office on Apr. 2, 1999 along the filing of the instant application.

TECHNICAL FIELD

The present invention relates to methods of detecting or measuring viruses and reagents therefor.

BACKGROUND ART

Currently, various methods of detecting viruses have been used to detect the presence of infectious viruses in blood or blood products, and to identify the presence of viruses in patients with diseases. However, these methods are not always highly sensitive or specific though the sensitivity and the specificity may vary with the type of virus to be detected. Even when they are sensitive and specific enough, they are often expensive and require lengthy procedures as in the culture and isolation of a virus. As a background to the present invention, type C hepatitis (hepatitis C) will be mentioned in detail below.

The causative agent of hepatitis C had long been unknown, but when the gene of the virus was cloned (Science 244: 359-362, 1989) and a diagnostic method by antibody measurement using a recombinant antigen generated based on said gene was developed (Science 244: 362-364, 1989; Japanese Patent Publication (Kohyo) 2 (1990)-500880), it was found that hepatitis C is an infectious disease whose causative agent is hepatitis C virus (HCV) that is transmitted through the blood and blood products as its main route of infection. With the development of the so-called second generation antibody testing method in which a recombinant core antigen and a recombinant NS3 antigen have been added, it is now possible to identify virtually all HCV patients by testing their serum. This has made it possible to eradicate almost all HCV infections transmitted though blood donations in Japan.

However, as for other common viral infections such as by the human immunodeficiency virus (HIV), there is a period of time until the appearance of antibodies after infection, or the so-called window period in which a virus is unidentifiable by existing testing methods. This means that the risk of secondary infection is still present, due to blood-borne components that cannot be identified by antibody testing methods, in areas where blood-selling is legal or in some regions of Japan. The antibody testing method also has a drawback in that it cannot distinguish a person who has recuperated from an infection and a person who is in the active stage of infection because of its principle of testing.

Interferon (IFN) is currently used for the treatment of hepatitis C. Some researchers insist, however, that the efficacy of the therapy can be evaluated by only measuring the antibody titer of HCV because the titer declines 6 months after elimination of HCV by IFN. However, since the antibody titer starts to decline only after the reduction of antigen stimulation or several months after the elimination of antigen, it is impossible to determine whether IFN administration resulted in the elimination of HCV, at a desired timing and accuracy, by the antibody testing alone. Hence, in order to monitor the therapy, it is necessary to detect HCV per se in addition to the HCV antibody.

It was difficult to establish a method of directly detecting the virus particle (virus antigen) of HCV because blood levels of the virus are very low as compared to other viruses such as hepatitis B virus (HBV) and because the virus cannot be propagated in vitro or using an animal etc. as a host. Therefore, instead of detecting the virus antigen, methods of detecting the genomic RNA of the virus were developed such as the polymerase chain reaction (PCR) method (Science 230: 1350-1354, 1985) and the branched-chain DNA probe method. But, the method of detecting viral genomes have several problems when compared to the method of detecting virus antigens.

First, it has been pointed out that since the substance to be detected is RNA that is not very stable during storage, the procedure of freezing and thawing of serum may cause a reduction in the measured value. Thus, the serum samples to be tested must be stored more carefully than when they are used in other assay methods. Utmost care must also be taken in transportation of the samples.

Although the testing methods that involve the use of a PCR method are the most sensitive for detecting gene fragments, they have problems in that: reverse transcription from a genomic RNA to a template DNA is often accompanied by losses, which therefor requires great skills to obtain an accurate quantitative value, and: since amplification is an important principle in the methods, a high incidence of false-positives may occur in case of contamination, and thus the processing of a large volume of samples at one time is impossible. Furthermore, even those methods which are postulated to be a simple procedure take 2 hours or more for pretreatment of samples and are complicated since repeated procedures of centrifugation and the like are required. In addition, such complicated procedures lead to increased chances of contamination and thereby increased chances of obtaining false-positive results. On the other hand, the branched-DNA probe method is low in detection sensitivity and besides takes about 20 hours before obtaining test results (Igaku to Yakugaku [Medicine and Pharmacology] 31: 961-970, 1994), and hence the method leaves much to be desired in terms of sensitivity and processing time.

In order to solve the above-mentioned problems associated with the methods of detecting viral genomes, methods were developed that involve the direct detection of a virus antigen. As shown in Japanese Unexamined Patent Publication (Kokai) No. 8 (1996)-29427, a method was developed that detects the core antigen of HCV in the serum using monoclonal antibody specific for the core antigen. As has been reported in Tanaka et al., Journal of Hepatology 23: 742-745, 1995, and Fujino et al., Igaku to Yakugaku [Medicine and Pharmacology] 36: 1065-1070, 1996, methods of detecting the core antigen in the serum have been shown to have a clinical usefulness as do the above-mentioned methods of detecting the viral genome. However, there are still several major problems that need be solved as in the methods of detecting the viral genome.

One such problem is that the sensitivity, compared to the PCR method, is so low that it cannot be used as a final test method of serum screening. Tanaka et al., Journal of Hepatology 23: 742-745, 1995, indicated that the detection limit is $10^4$-$10^5$ copies/ml of HCV RNA. Fujino et al., Igaku to Yakugaku [Medicine and Pharmacology] 36: 1065-1070, 1996, reported that the method has shown a positive rate of 67% on 102 sera of the patients before treatment with chronic hepatitis C who were found to be RNA positive by the most sensitive detection method of CRT (competitive reverse transcription)-PCR method. That is, in terms of sensitivity, the method lags far behind the most sensitive CRT-PCR method.

Furthermore, the complicated procedure of treating samples for measurement, and the long time it takes, pose problems when it is used in screening. Thus, the method requires a multi-step procedure for sample (serum) treatment comprising: a polyethylene glycol treatment (4° C., 1 hr) for the concentration of virus particles and the removal of serum components; centrifugation (15 min); the removal of supernatants; urea treatment; the alkali treatment (37° C., 30 min); the addition of the neutralizing agent and the like. In addition, the process of dispersing, with urea, the precipitate having an increased viscosity due to the PEG treatment requires great skill. In order to obtain a reproducible result, therefore, great skill is required and, besides, a minimum of 2 hours of treatment is necessary. Furthermore, such processes as centrifugation, supernatant removal, etc. are not amenable to automation and render the simultaneous treatment of a large number of samples very difficult. Thus, from a viewpoint of ease of handling as well, the method is not suited for applications that require the treatment of a large volume of samples as in screening tests.

On the other hand, the virus antigen detection system is superior to the highly sensitive PCR method in the following points. Thus, it is very tolerant to contamination because it involves no procedure of excessive amplification in the detection step. Furthermore, since it is intended to detect antigen protein that is relatively stable instead of poorly stable RNA, it requires no excessive care in the storage of samples, it does not require special equipment such as the deep freezer that is needed for samples to be detected by PCR, and the transportation of the samples is also easier.

These features are suitable for applications in which a large number of samples is measured as in the blood industry or health checkup testing. However, because the disclosed method of detecting the core antigen, as indicated above, is not amenable to automation and is low in sensitivity so that it cannot be a gold standard in applications that require high sensitivity such as in the blood industry, it cannot be applied to tests that handle a large number of samples such as screening, and cannot make the best use of its advantageous features over the PCR method. Furthermore, clinically useful assay methods must always face the challenges of sensitivity, specificity, reproducibility, ease of handling, and low cost, and sustained efforts are needed to satisfy these challenges as much as possible. With regard to detection of virus antigens other than HCV, especially for use in screening handling a large number of samples, there are many methods that are not put into practical use because they are low in sensitivity, as compared to the PCR method, or the desired antigen could not be fully exposed.

DISCLOSURE OF THE INVENTION

It is an object of the present invention to provide a method for detecting various virus antigens, including a method for detecting HCV antigen, that is suitable for treating a large number of samples as in screening in the blood industry and health checkups. In other words, the object of the present invention is to provide the detection system for various virus antigens including a method of detecting HCV antigen that has a sensitivity and specificity equivalent to those of the PCR method, that permit simple pretreatment, or that can be easily automated without pretreatment. Preferred embodiments of the present invention will now be explained hereinbelow with a main reference to HCV.

According to the first embodiment (1) of the present invention, there is provided a means to detect or determine HCV by disrupting the virus particle, fully exposing the virus antigen, disrupting antibodies, if present, against the virus antigen, and detecting or determining the virus antigen.

Thus, the present invention provides (I) a method for treating a virus-containing sample, characterized by treatment of a virus-containing sample with a treatment solution containing (1) an anionic surfactant and (2) an amphoteric surfactant, nonionic surfactant, or protein denaturant.

The present invention also provides (II) a method for treating a virus-containing sample, characterized by treatment of a virus-containing sample with a treatment solution containing (1) an anionic surfactant, (2) an amphoteric surfactant and (3) a nonionic surfactant or protein denaturant.

The present invention also provides (III) a method for treating a virus-containing sample, characterized by treatment of a virus-containing sample with a treatment solution containing (1) an anionic surfactant, (2) an amphoteric surfactant, (3) a nonionic surfactant and (4) a protein denaturant.

The present invention also provides (IV) a virus assay method characterized by using a sample treating method according to any one of (I) to (III) and reacting a sample with a probe which specifically recognizes a virus antigen, for detection or quantitation of the presence of the virus antigen.

The present invention also provides a kit, assay kit or diagnostic reagent for determining the presence or absence of a virus in a sample, which is for use in the above (IV) immunoassay method and comprises an anionic surfactant.

The present invention also provides a kit, assay kit or diagnostic reagent for determining the presence or absence of a virus in a sample, which is for use in the above (IV) immunoassay method and comprises a monoclonal antibody described hereinbelow.

According to the first embodiment (2) of the present invention, there is provided a means to detect or determine a virus by disrupting the virus particle, fully exposing the virus antigen, disrupting antibodies, if present, against the virus antigen and detecting or determining the virus antigen.

Thus, the present invention provides (V) a method for treating a virus-containing sample, characterized by treatment of a virus-containing sample with a treatment solution containing (1) a chaotropic ion and (2) an acidifying agent.

The present invention further provides (VI) a method for treating a virus-containing sample, characterized by treatment of a virus-containing sample with a treatment solution containing (1) an chaotropic ion, (2) an acidifying agent and (3) a nonionic surfactant.

The present invention further provides (VII) a virus assay method, characterized by using a sample treating method according to the above (V) and (VI) and reacting a sample with a probe which specifically recognizes a virus antigen, for detection or quantitation of the presence of the virus antigen.

The present invention further provides a kit, assay kit or diagnostic reagent for determining the presence or absence of a virus in a sample, which is for use in the above (VII) method and comprises a chaotropic agent.

The present invention further provides a kit, assay kit or diagnostic reagent for determining the presence or absence of HCV in a sample, which is for use in the above (VII) method and comprises a monoclonal antibody produced by a hybridoma HC11-14 (FERM BP-6006), HC11-10 (FERM BP-6004) or HC11-11 (FERM-BP-6005).

According to the second embodiment of the present invention, there is provided a method to detect or determine a virus antigen during the window period in which antibodies against said virus have not yet been generated. In this method, the disruption of the virus particle to expose the virus antigen is sufficient and there is no need to disrupt antibodies against the virus antigen in the blood.

Thus, the present invention provides a virus assay method characterized by measurement of a virus antigen based on its binding with a probe in the presence of a surfactant with an alkyl group of 10 or more carbon atoms and a secondary, tertiary or quaternary amine, or a nonionic surfactant with a hydrophilic/lipophilic balance (HLB) of 12-14, or of both of them.

The present invention further provides a hybridoma cell line selected from the group consisting of HC11-11 (FERM-BP-6005), HC11-14 (FERM BP-6006), HC11-10 (FERM BP-6004), HC11-3 (FERM-BP-6002), and HC11-7 (FERM-BP-6003).

The present invention also provides a monoclonal antibody produced by a hybridoma cell line selected from the group consisting of HC11-11 (FERM BP-6005), HC11-14 (FERM BP-6006), HC11-10 (FERM BP-6004), HC11-3 (FERM BP-6002), and HC11-7 (FERM BP-6003).

Furthermore, HCV which is an RNA virus, and HBV which is a DNA virus, are viruses which form virus particles having a structure comprising a structural protein encapsulating genomic RNA or DNA and a membrane protein or lipid membrane surrounding it. In either embodiment, by using a treating method of the present invention, there is provided detection or determination of a virus characterized by disrupting a virus particle of not only HCV or HBV but also a virus having similar a structure thereto, by fully exposing the virus antigen, and by detecting or determining said antigen.

BEST MODE FOR CARRYING OUT THE INVENTION

Figure 1:
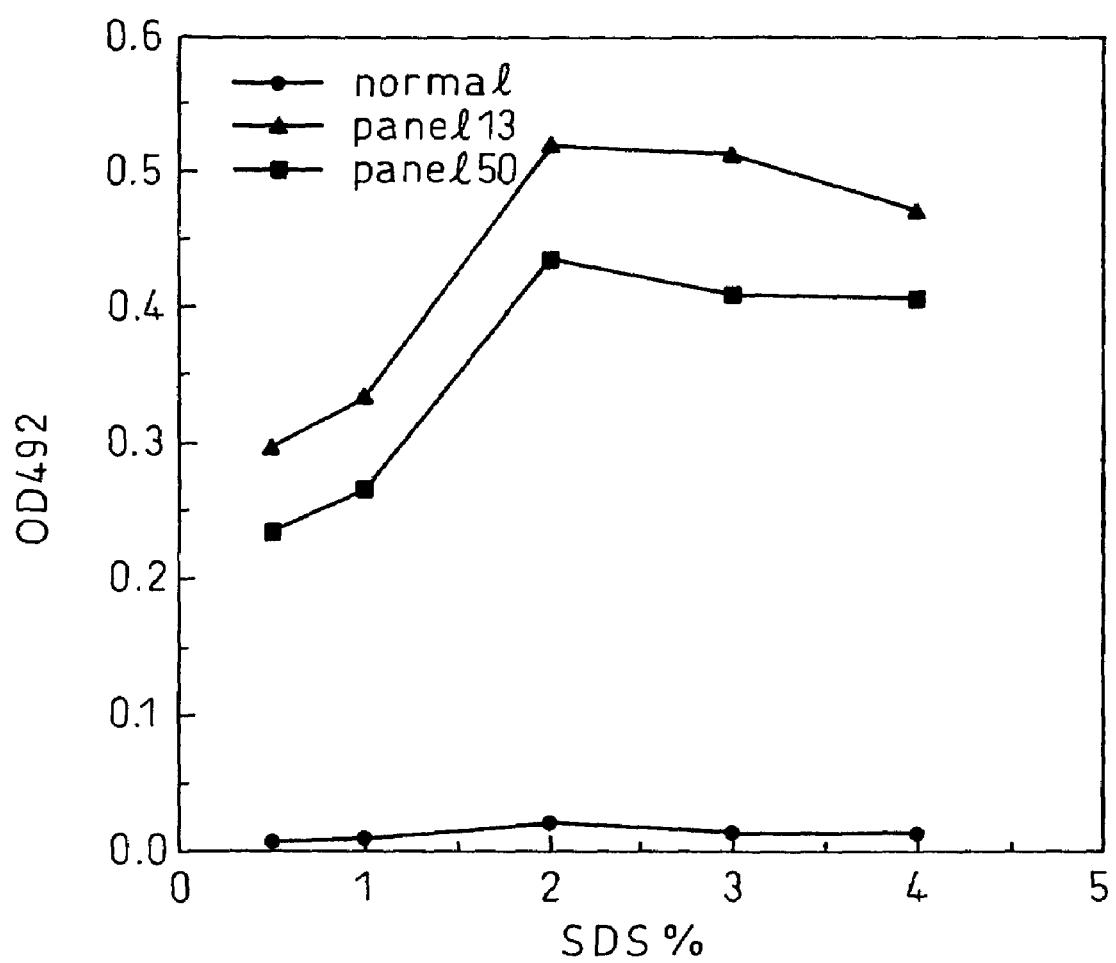
FIG. 1 is a graph showing the effect of concentration of added SDS on sample treatment. Sera from normal healthy human subjects (normal) and HCV-RNA-positive panel sera 13 and 50 were used.

The subject viruses of the present invention are viruses which form virus particles having a structure comprising a structural protein encapsulating genomic RNA or DNA and a membrane protein or lipid membrane surrounding it.

Representative examples of the above viruses having RNA as a genome include hepatitis C virus (HCV) and HCV-related viruses.

HCV-related viruses include hepatitis D virus, hepatitis E virus, hepatitis G virus, hand-foot-and-mouth disease virus, a flavivirus (yellow fever virus, West Nile virus, Japanese encephalitis virus, dengue virus), a togavirus (alpha-virus, rubivirus, arterivirus, rubella virus), a pestivirus (hog cholera virus, bovine diarrhea virus), a paramyxovirus (parainfluenza virus 1, 2, 3, 4, canine distemper virus, Newcastle disease virus, RS virus, rinderpest virus, simian parainfluenza virus, measles virus, mumps virus), an orthomyxovirus (human influenza virus, avian influenza virus, equine influenza virus, swine influenza virus), a rhabdovirus (rabies virus, vesicular stomatitis virus), a picornavirus (poliovirus, Coxsackie virus, echovirus, bovine enterovirus, porcine enterovirus, simian enterovirus, mouse encephalitis virus, human rhinovirus, bovine rhinovirus, equine rhinovirus, foot and mouth disease virus, hepatitis A virus), a coronavirus (human coronavirus, avian infectious bronchitis virus, mouse hepatitis virus, porcine transmissible gastroenteritis virus), an arenavirus (lymphocytic choriomeningitis virus, lassa virus, Korean hemorrhagic fever virus), a retrovirus (HTLV: human adult leukemia virus, HIV: AIDS virus, feline leukemia sarcoma virus, bovine leukemia virus, Rous sarcoma virus), a reovirus (rotavirus), a calcivirus (Norwalk virus), a bunyavirus (renal syndrome hemorrhagic fever virus), a phyllovirus (Ebola virus, Marburg virus), and the like.

Representative examples of the above viruses having DNA as a genome include hepatitis B virus HBV) and HBV-related viruses. HBV-related viruses include a pox virus (vaccinia virus, alastrium virus, cowpox virus, smallpox virus), a parvovirus (human parvovirus, porcine parvovirus, bovine parvovirus, canine parvovirus, feline leucopenia virus, Aleutian mink disease virus), a papovavirus (papilloma virus, polyoma virus), adenovirus, a herpes virus (herpes simplex virus, cytomegalovirus, chickenpox herpes zoster virus, EB virus, equine herpes virus, feline herpes virus, Marek's disease virus), African swine cholera virus, and the like.

In addition to the above, there are many pathogenic viruses known and there are many unidentified viruses present. It is clear that if such viruses have a structure described above comprising a structural protein encapsulating genomic RNA or DNA and a membrane protein or lipid membrane surrounding it, they can be released in a form suitable for immunoassay using the sample treating method of the present invention.

Embodiments for carrying out the present invention will now be explained below referring to HCV. Since blood levels of HCV are $10^2$ copies/ml to $10^6$ copies/ml which are lower than those of HBV ($10^9$ copies/ml), a very high sensitivity is required for an assay to detect the virus antigen.

Generally, in a detection method represented by an immunological method that uses antibody as a probe, possible methods to enhance detection sensitivity include I) an increase in the number of the antigen molecules to be detected, II) an increase in the number of molecules of the probe, for example antibody, that binds to the antigen, III) a reduction in nonspecific reactions that define detection sensitivity caused by the binding of the probe, for example antibody, with a substance other than the antigen, and IV) an increase in the detection limit of a label for use in the detection, and an appropriate combination of these methods would enable an increase in sensitivity.

As a method to increase the number of antigen molecules, I-1) an increase in the amount of sample is most easily conceived. But, since the maximum amount to be added in a commonly used reaction system (for example, a 96-well immunoplate) cannot exceed about 300 µl, I-1), a concentration method to increase the number of molecules to be added to the reaction system has been used.

In order to increase the number of probes, for example antibody molecules, that bind to the antigen, the most readily conceived means includes II-1) an increase in the number of epitopes to be recognized using multiple probes, for example antibodies, and II-2) an increase in the number of antibodies bound per unit time by increasing the affinity (affinity and avidity) of the probe, for example antibody, with the antigen.

Incidentally, possible methods to enhance the affinity of, for example, antibody include a method of changing the composition of the buffer in the reaction system, a method of altering the probe, and a method of combining these. II-3) Methods are also conceived in which many antigens are captured by binding a large number of antibodies to the carrier having a wide surface area such as beads, magnetic particles, etc. to expand the reaction area with a limited amount of antigen.

In the case of infectious diseases, human antibodies having a high affinity of binding to antigen are expected to be present in the sample. Accordingly, it is expected that the epitopes of these antibodies overlap with those of the probes, for example antibodies, to be used in the detection, resulting in a competitive reaction that causes a reduction in the number of antibodies to be used for detection. It is, therefore, anticipated that a reduction in these interfering antibodies in the sample leads to an increase in the number of antibody molecules for use in detection that bind to antigen (II-3).

It is indeed difficult to generalize the methods of reducing nonspecific reactions, but strategies are conceived that reduce nonspecific reactions III-1) to reduce nonspecific reactions by increasing the affinity (affinity and avidity) of the probe, for example antibody, with the antigen by changing the composition of the buffer solution, III-2) to remove the causative agent of the nonspecific reactions, and the like.

Possible methods to enhance detection sensitivity include: IV-1) to employ a label (a radioisotope, etc.) having a high detection sensitivity; IV-2) to amplify signals by employing an enzyme or a catalyst as a label; IV-3) to change an enzyme substrate into one having a higher sensitivity; IV-4) to amplify signals from an enzymatic reaction or a chemical reaction by an electrical or a mechanical means; IV-5) to increase the number of labels per antibody; IV-6) to enhance the sensitivity of the instrument used for signal detection, and the like.

Analysis of the steps of pretreatment in the disclosed method for detecting the HCV core antigen revealed that the method comprises the step of concentrating the antigen by adding polyethylene glycol to the sample which is then centrifuged to recover HCV as a precipitate (1-2) and simultaneously removing part of the serum components (II-2), followed by the step of resuspending the precipitate in a solution containing urea and the alkali agent to inactivate human antibody present therein thereby releasing core antigen from HCV (II-3), and the step of adding a solution containing a nonionic surfactant (Triton X100) and a neutralizing agent to prepare a solution which is to be reacted with the monoclonal antibody.

As described above, centrifugation and resuspension of the precipitate are procedurally complicated steps and require great skill. Thus, a goal of the present invention is a core antigen detection system that resolves the above problems concerning procedures.

The identity of HCV per se has not been elucidated yet. But, based on the genomic structure, the structures of related virus particles, and general information on viruses, it is estimated that an HCV particle has a genomic RNA that is packed within the core antigen, which in turn is encapsulated by a coat protein comprising E1 and E2/NS1 antigens that are anchored to a lipid membrane surrounding the above packing.

It is therefore necessary to remove the coating to thereby permit the binding of a probe, for example an antibody, to be used for detection of said core antigen in order to detect core antigen. Furthermore, it has been reported that the virus particle in the blood takes a complex structure in which the particle is surrounded by LDL (low density lipoprotein) etc., and since antibodies against the coat protein are also present, it is estimated that the virus particle may be present as an immune complex with an anti-coat protein antibody. Thus, in order to increase the number of antigen molecules to be detected, it is important to efficiently remove from the virus particle the coating and contaminants surrounding the virus particle, and to efficiently release the core antigen molecules.

The same holds true for viruses other than HCV and the structural proteins of viruses must be efficiently released.

Thus, the present invention relates to a treating method that brings a virus antigen in a sample (serum) to a state suitable for detection using a probe, without concentrating the antigen by a complicated procedure such as centrifugation.

Furthermore, since a human antibody may be present, as described above, at a high titer that competes with a probe, for example antibody, for binding, a procedure to remove said antibody is important to enhance sensitivity.

Thus, one embodiment of the present invention relates to a treating method that easily releases virus antigens in a sample, concurrently inactivating human antibody that may be present in the sample.

By using the treating method of the present invention, virus antigens in a sample is released from a virus particle or an immune complex in a form suitable for forming an immune complex with a probe such as antibody, and by simultaneously inactivating human antibody present in the sample that interferes with the detection reaction, a highly sensitive detection can be readily attained by an immunoassay using a probe such as antibody.

According to the first embodiment (1) of the present invention, a probe such as antibody for use in detection may be any probe, as long as it binds to the virus antigen in a specific manner, it has a certain high affinity, and it does not induce nonspecific reactions when added to the reaction system. For example, in the detection of a HCV core antigen, as described in Example 4, one of the probes used in the primary reaction preferably contains a probe that can recognize and bind to the C-terminal of the HCV core antigen. The C-terminal of the core antigen as used herein means a sequence from 81 to 160 of the sequence shown in SEQ ID NO: 2 or a part thereof. It can also contain a probe for the N-terminal of the HCV core antigen. The N-terminal of the core antigen as used herein means a sequence from 10 to 70 of the sequence shown in SEQ ID NO: 2 or a part thereof.

According to the second embodiment (2) of the present invention, a probe such as antibody for use in the detection may be any probe, as long as it binds to the virus antigen in a specific manner, it has a certain high affinity, and it does not induce nonspecific reactions when added to the reaction system. For example, in the detection of the HCV core antigen, one of the probes used in the primary reaction preferably contains a probe that can recognize and bind to the N-terminal of the HCV core antigen. The N-terminal of the core antigen as used herein means a sequence from 10 to 70 of the sequence shown in SEQ ID NO: 2 or a part thereof. It can also contain a probe for the C-terminal of the HCV core antigen. The C-terminal of the core antigen as used herein means a sequence from 81 to 160 of the sequence shown in SEQ ID NO: 2 or a part thereof.

In any of the above embodiments, any molecule that has a high specificity and affinity for the core antigen can be used as a probe, including: a monoclonal antibody obtained by immunizing an experimental animal such as a mouse, a rabbit, a chicken, a goat, sheep, a bovine, etc., a monoclonal antibody produced by a hybridoma obtained by the fusion of a myeloma cell with a spleen cell that was isolated from an immunized individual, a monoclonal antibody produced by a spleen cell or leukocyte in the blood immortalized by the EB virus, and an antibody produced by a human or a chimpanzee infected with HCV; a recombinant antibody produced by a cell transformed with a recombinant antibody gene generated by combining a gene fragment of a variable region obtained from the cDNA or chromosomal DNA of immunoglobulin of a mouse, a human, etc., a gene fragment of the variable region constructed by combining a part of the cDNA or chromosomal DNA of immunoglobulin with an artificially constructed sequence, a gene fragment of the variable region constructed using an artificial gene sequence, or a gene fragment of the variable region constructed by a gene recombinant technology using the above as building blocks, with a gene fragment of the immunoglobulin constant region; a phage antibody generated by the fusion of a gene fragment described above of the variable region with a structural protein of, for example a bacteriophage, a recombinant antibody produced by a cell transformed with a recombinant antibody gene generated by combining a gene fragment described above of the variable region with part of another suitable gene fragment, for example myc gene, a probe produced by artificially introducing a variable region into the trypsin gene, a probe obtained by artificially altering a molecule that specifically binds to the protein such as receptor, a probe constructed by the combinatorial chemistry technology, and the like.

The present invention further provides the step of treating a sample with a treatment solution capable of releasing a virus antigen from a virus particle or an immune complex and of simultaneously inactivating even a human antibody present in the sample that interferes with the detection reaction in order to generate a state suitable for forming an immune complex of the above virus antigen and a probe thereof such as an antibody from a sample containing the virus antigen, and an assay method and an assay kit for detection and quantitation of the released core antigen by an immunoassay using a probe such as antibody.

The Sample Treatment Solution and the Sample Treating Method Provided by the Present Invention Samples as used herein include biological fluids such as whole blood, plasma, serum, urine, saliva, cerebrospinal fluid, liver tissue and the like.

According to the present invention, the most important requirement is a method of treating a virus antigen such as the core antigen in a sample so as to generate a state suitable for a binding reaction with the probe such as monoclonal antibody without the complicated processing of a sample. Thus, in order to increase the number of antigen molecules, it is important to efficiently release the virus antigen such as the core antigen contained in a virus particle.

As has already been known for sodium dodecyl sulfate (SDS) polyacrylamide gel electrophoresis (SDS-PAGE), most proteins are denatured by heat treatment in the presence of SDS and thereby molecules other than the covalently-bound ones are converted into monomers. Thus, the addition of a treatment agent comprising an anionic surfactant such as SDS causes disruption of viruses as well as the denaturing of antibodies against the virus antigen such as the core antigen in the sample, enabling the release of the virus antigen such as the core antigen in the sample. This was also confirmed for the HCV core antigen as shown in Example 7, that is, when the core antigen in a HCV-infected sample treated with a treatment agent containing SDS was subjected to a molecular weight analysis using gel filtration, it was detected at a position that is theoretically predicted to be the position of the monomer.

As reported by Kashiwakuma et al., J. Immunological Methods 190: 79-89, 1996, when the core antigen isolated by SDS-PAGE from a sample comprising an extract of a cell expressing recombinant HCV is detected using a Western blot analysis, the immunological activity is detected at a position believed to be that of the monomer. It is readily understood by a person skilled in the art that the addition of a denaturant comprising SDS to a sample causes efficient release of antigens and an increase in the number of antigen molecules.

As is well known, however, anionic surfactants such as SDS have a very strong protein-denaturing effect so that when added to a reaction of immune complex formation with the antibody they also denature the antibody and thereby disrupt the function resulting in the reduction in sensitivity. It is also known that the structure of epitopes are destroyed by the treatment with an anionic surfactant causing a weakened bonding with the antibody and a reduced sensitivity. In order to remove the factors responsible for the reduction in sensitivity, the denaturing effect following SDS treatment need to be weakened by some means or other.

It is known that surfactants comprising anionic surfactants may be removed by such means as dialysis, ultra-filtration, gel filtration, electrophoresis, ion exchange, precipitation, membrane transfer, etc. The fact that, as described above, antigens can be detected by a Western blot method or gel filtration method indicates that an antigen-antibody reaction may be effected using a certain procedure following the SDS treatment. However, these methods require both time and complex procedures, which is not suitable for the purpose of the present invention.

By diluting with an excess amount of the reaction solution, it is indeed possible to reduce the denaturing effect to a negligible level that does not affect the reaction, but the method cannot be applied to the methods such as an immunoassay that involves the use of microtiter wells in which the amount of samples to be added is limited. In this regard, it is evident that these methods are not suitable for the purpose of the present invention.

Thus, the inventors of the present inventors have investigated, in the first embodiment of the present invention, whether the addition of a treatment agent comprising an anionic surfactant and some additive could reduce the denaturing effect by the anionic surfactant to a level in which the probe such as antibody is not affected, and, at the same time, enhance the releasing effect of the core antigen by the anionic surfactant.

The inventors of the present invention have found that the addition of a treatment agent containing a surfactant other than an anionic surfactant such as SDS can weaken the denaturing effect of SDS on the immobilized antibody and, as a result, can enhance sensitivity as compared to the addition of a treatment agent containing SDS alone. The inventors have also found that when the agents that weaken the hydrogen ion bonding such as a surfactant other than SDS and urea are added to the treatment agent containing an anionic surfactant such as SDS, similar effects were observed, and that the release of the core antigens from the virus particles and the inactivation of the anti-core antigen antibody in the sample were enhanced with a result that the release of the core antigens was further enhanced. The inventors have also found that the detection of the core antigen with a higher sensitivity was attained by a heat treatment after the addition of a treatment agent containing SDS and other surfactants, and have completed the present invention.

The anionic surfactants other than SDS that can be used for the treatment of samples include sodium cetyl sulfate or other alkyl sulfate esters, alkyl sulfonates such as sodium dodecyl sulfonate, alkyl allyl sulfonates, and the like. The surfactants other than the anionic surfactants that can be added include amphoteric surfactants, for example CHAPS (3-[(3-cholamidopropyl)dimethylammonio]-1-propanesulfonate), CHAPSO (3-[(cholamidopropyl)dimethylammonio]-2-hydroxy-1-propanesulfonate), dodecyl-N-betaine, 3-(dodecyldimethylammonio)-1-propanesulfonate; nonionic surfactants, for example polyoxyethylene isooctylphenyl ethers such as Triton X100, polyoxyethylene nonylphenyl ethers such as NP 40, polyoxyethylene sorbitol esters such as Tween 80, polyoxyethylene dodecyl ethers such as Brij 58, and octyl glucoside, with an amphoteric surfactant such as CHAPS and an nonionic surfactant such as Triton X100 being preferred. It is also advantageous to add an agent (protein denaturant) that disrupts higher structures of proteins such as urea, thiourea, and the like.

Concentrations preferably used in the treatment are: 0.5% or greater for SDS; 0.1% or greater for CHAPS; 1M or greater for urea; 0.1% or greater and 0.75% or smaller for Triton X100.

The temperature used for the treatment of samples may be any temperature commonly used in the laboratory, i.e. between 4° C. and 100° C., but when a nonionic surfactant is added care should be taken as to its cloud point. Preferably a temperature of 37° C. or greater is employed and the treatment at a temperature of 50-60° C. that is commonly used for the inactivation of the serum is more effective.

Removal of Interference by Hemoglobin

When serum etc. is used as a sample for measurement, red blood cells contained in said sample undergo hemolysis during the above pretreatment and hemoglobin is released, and the denatured hemoglobin may interfere with measurement by binding to the virus antigen such as the HCV core. Thus, in the first embodiment of the present invention, it is preferred to remove the interference with measurement by capturing the heme in the hemoglobin. As an additive for this purpose, we have found that the addition of at least one of urea and a compound containing an imidazole ring is preferred.

As the imidazole ring-containing compounds, there may be mentioned imidazole, histidine, imidazoleacrylic acid, imidazolecarboxyaldehyde, imidazolecarboxamide, imidazoledione, imidazoledithiocarboxylic acid, imidazoledicarboxylic acid, imidazolemethanol, imidazolidinethione, imidazolidone, histamine, imidazopyridine, and the like.

As the indole ring-containing compounds, there may be mentioned tryptophan, indoleacrylic acid, indole, indoleacetic acid, indoleacetic hydrazide, indoleacetic methyl ester, indolebutyric acid, indoleacetonitrile, indolecarbinol, indolecarboxaldehyde, indolecarboxylic acid, indoleethanol, indolelactic acid, indolemethanol, indolepropionic acid, indolepyruvic acid, indolyl methyl ketone, indolmycin, indoleacetone, indomethacin, indoprofen, indoramine, and the like.

The amount added is preferably 0.5M to 5M for urea, 5 mM to 50 mM for indoleacrylic acid, and 0.05M to 0.5M for the other additives.

On the other hand, membrane proteins such as the HCV coat protein do not dissolve spontaneously unless they are treated to that end. In order to dissolve a protein having a hydrophobic portion in water, the method of converting a hydrophobic portion into a hydrophilic portion with a surfactant is well known. It is known, however, that certain salts such as guanidine chloride have a property of making refractory proteins water-soluble. Ions produced from salts (chaotropic agents) having such a property are called chaotropic ions, and as the anionic ions, guanidine ions, thiocyanate ions, iodine ions, periodate ions, perchlorate ions, and the like are known. Salts that generate these ions have been used for solubilization of refractory proteins. It was estimated that chaotropic ions have a function of efficiently releasing the antigens from the virus particles.

When a chaotropic ion is added, however, the secondary structure of proteins is disrupted causing the destruction of the epitope structure. Thus, when a probe such as antibody is added for the reaction of immune complex formation in the presence of a chaotropic ion as it is, binding with the antibody is weakened and the sensitivity decreases, which are thought to pose a serious problem.

On the other hand, the denaturing effect of chaotropic ions is mostly reversible, so that by weakening ionic strength by dialysis or dilution the denatured structure temporarily returns to the original structure. This poses another problem associated with the use of a treatment agent such as a chaotropic ion. That is, according to the desired treating method of the present invention, not only the virus particles present in the sample are efficiently released, but the high-affinity antibody that binds to the antigen present in the sample must be inactivated at the same time. Thus, solubilization with a chaotropic ion does not provide an adequate inactivation of the high-affinity antibody present in the sample, and, it is believed, the antibody adversely affects sensitivity.

Thus, the treating methods that employ chaotropic ions have two conflicting problems: in the condition in which a chaotropic ion can destroy a structure, the antigen-antibody reactions are inhibited, and on the other hand the effect of a chaotropic ion alone is not sufficient to inactivate antibodies that interfere with reactions in the sample, and in the condition in which the antigen-antibody reactions are not inhibited, contaminating antibodies can inhibit the reactions.

In order to solve these conflicting problems it is necessary to find a condition in which the epitopes of the antigen are destroyed reversibly and the functions of the contaminating antibodies in the sample are destroyed irreversibly.

As to the conditions in which antibody is inactivated, an alkali treatment, an acid treatment and the like are known. The acid treatment of serum can cause false-positive results since the treatment irreversibly denatures some of serum proteins resulting in the formation of precipitates that in most cases hinder pipetting after the treatment of samples, and precipitates that engulfed the denatured proteins are adsorbed to the solid phase at the time of measurement and thereby may be detected as a density. In addition, another problem arises because when the antigen of interest is nonspecifically engulfed in the precipitate, the amount of antigen that reacts with the probe decreases resulting in a decrease in sensitivity.

The inventors of the present invention have found that the acid treatment combined with the guanidine treatment can resolve the problems associated with the acid treatment such as precipitate formation and the conflicting problems associated with the guanidine treatment, and thereby have completed the present invention. We have also found that it is further preferred to add a surfactant to the treatment agent comprising a chaotropic ion such as guanidine and an acidifying agent. As the acidifying agent, hydrochloric acid, sulfuric acid, acetic acid, trifluoroacetic acid, trichloroacetic acid, and the like are preferred.

As the surfactant, an amphoteric surfactant such as CHAPS (3-[(3-cholamidopropyl)dimethylammonio]-1-propanesulfonate), CHAPSO (3-[cholamidopropyl)dimethylammonio]-2-hydroxy-1-propanesulf onate), dodecyl-N-betaine, 3-(dodecyldimethylammonio)-1-propanesulfonate, or the like, and a nonionic surfactant such as a polyoxyethylene isooctylphenyl ether, for example Triton X100; a polyoxyethylene nonylphenyl ether, for example NP 40; a polyoxyethylene sorbitol ester, for example Tween 20; a polyoxyethylene dodecyl ether, for example Brij 58; octyl glucoside, or the like is preferred. Furthermore, an agent such as urea that partially destroys a higher structure of proteins by weakening hydrogen ion bonding may be added therein.

Especially, it is more preferred to use guanidine hydrochloride at 2 M or greater, Triton X100 at 2% or greater, and Tween 20 at 0.02% or greater at a temperature of 4° C. to 45° C.

In any of the embodiments, it is evident that a virus antigen can be released in the form of a probe, i.e. a state suitable for the so-called immunoassay that uses antibody as a probe, from the sample containing virus particles having a structure similar to that of HCV or HBV by using the treating method of the present invention. Viruses having a structure similar to that of HCV or HBV as used herein are viruses that form virus particles having a structure composed of proteins in which the genomic RNA or DNA has been packed and the membrane protein or the lipid membrane surrounding it. The viruses include, for example, flaviviruses that are related to HCV, retroviruses such as human immunodeficiency virus (HIV), and the like. Furthermore, those having DNA as the genome like HBV are also included when they have a similar structure.

Exposure of Virus Antigen

According to the second embodiment of the present invention which relates to a method of detecting the virus antigen in a sample collected during the window period, antibody to the virus antigen has not been formed yet and so the disruption of the virus particle to expose the virus antigen is sufficient and there is no need to destroy antibodies present in the sample. Thus, pretreatment of samples described above is not necessary and the presence of a virus particle-disrupting agent to expose the virus particle is sufficient. Especially, the virus particle-disrupting agent is essential for the virus antigens present in the virus particle.

It is believed that virus particles in general have a structure in which a nucleic acid as the genome and a core antigen form a complex forming a particle and said particle is coated by a coat comprising a lipid membrane and an envelope protein. It is also believed that in the blood they are present in the form of a complex with a low density lipoprotein, an antibody to the virus, and the like. Thus, a probe cannot recognize or bind to the virus antigens, specifically the antigens in the virus particle, with the particles as they are present in the blood. In order to detect the virus antigens, therefore, they must be treated by, for example, removing these structures surrounding the virus particle so that the virus particle can be recognized by a probe.

Thus, the present invention also provides a reaction condition under which the virus antigen in the virus particle contained in the sample is exposed so as to be recognized by the probe for recognizing the virus particle, a method of the reaction comprising the system of performing the reaction, and a reagent containing the system of performing the reaction.

A reaction system suitable for antigen detection in the system provided by the present invention comprises a condition which is mild enough to retain the function of the antibody against the epitopes of the virus antigen but which can fully expose the area recognized by the antibody, a virus antigen-recognizing probe, from the virus particle which is a complicated structure present in the sample.

For HCV, it has already been demonstrated that the core antigen can be detected by treating the virus particles isolated by ultra-centrifugation (Takahashi et al., 1992, J. Gen. Virol, 73: 667-672) and HCV particles precipitated by aggregation with polyethylene glycol using a nonionic surfactant such as Tween 80 or Triton X100 (Kashiwakuma et al., 1996, J. Immunological Methods, 190: 79-89). In the former, however, the detection sensitivity is not high enough and there remains a question as to whether the antigen has fully been exposed. In the latter also, the antibody has been inactivated by the addition of another treatment agent, and there is no mention of the effect of the surfactant per se.

According to the present invention, the conditions were first investigated centering on the surfactant. Accordingly, it was found that by using a composition based on the surfactant, an efficient detection of the antigen in the virus particle was attained, without employing any procedure of pretreatment such as centrifugation or heating, by only diluting the sample in the reaction solution.

It is necessary to effectively extract the virus antigens from the virus particles, and to suppress interactions with a variety of substances in the serum, thereby to provide a condition under which the probe can efficiently react with the antigen. As an effective surfactant used in this case, there may be mentioned a surfactant having both an alkyl radical of 10 or more carbons and a secondary, tertiary, or a quaternary amine in one molecule, or a nonionic surfactant.

In the above surfactant having an alkyl radical and a secondary, tertiary, or a quaternary amine, the alkyl group is preferably a straight-chain alkyl group and the number of carbon atoms therein is preferably 10 or greater, and more preferably 10 to 20. As the amine, a tertiary or quaternary amine (ammonium) is preferred. The specific surfactants include dodecyl-N-sarcosinic acid, dodecyl trimethyl ammonium, cetyltrimethyl ammonium, 3-(dodecyldimethylammonio)-1-propane sulfonate, 3-(tetradecyldimethylammonio)-1-propane sulfonate, dodecyl pyridinium, cetyl pyridinium, decanoyl-N-methyl glucamide (MEGA-10), dodecyl-N-betaine, and the like. Dodecyl-N-sarcosinic acid and dodecyl trimethyl ammonium are preferred.

As the nonionic surfactant mentioned above, those having a hydrophilic-lipophilic balance of 12 to 14 are preferred, and polyoxyethylene isooctylphenylethers such as Triton X100 and Triton X114, or polyoxyethylene nonylphenylethers such as Nonidet P40, Triton N101, and Nikkol NP are preferred.

According to the present invention, the above two types of surfactants may be used alone, but combined use of them is more preferable and a synergistic effect can be obtained by the combined use.

Additional components that change the aqueous environment such as urea may be added.

Monoclonal Antibody as a Probe in the Present Invention

The gene fragment of the structural protein of HCV as used herein means a gene fragment containing the core region of the structural protein of HCV and a DNA fragment having at least a base sequence encoding a polypeptide containing an amino acid sequence from 1 to 160 from the N-terminal of HCV. Specifically, it is a gene fragment comprising a base sequence encoding the amino acid sequence of SEQ ID NO: 2.

The polypeptide having the activity of HCV antigen as used herein means a fusion polypeptide or a polypeptide that immunologically reacts with the anti-HCV antibody, and can be used as an antigen for constructing a hybridoma and a monoclonal antibody obtained therefrom of the present invention. Specifically, it is a polypeptide having the activity of the HCV antigen comprising the amino acid sequence of SEQ ID NO: 1 or a polypeptide having the activity of the HCV antigen comprising a portion of the amino acid sequence of SEQ ID NO: 1, or a polypeptide having an additional amino acid sequence attached to the N-terminal or C-terminal thereof.

The monoclonal antibody of the present invention against the above fusion polypeptide and the polypeptide having amino acid sequences as shown in SEQ ID NO: 3-6 can be readily constructed by a person skilled in the art. The production of monoclonal antibody by a hybridoma is well known. For example, BALB/c mice may be periodically immunized intraperitoneally or subcutaneously with a fusion polypeptide or polypeptide (hereinafter referred to as the present antigen) mentioned above as a single antigen or as an antigen combined with BSA, KLH, or the like, singly or in a mixture with an adjuvant such as Freund's complete adjuvant. When antibody titer in the serum has increased, the present antigen is administered to the tail vein as a booster. After the spleen has been aseptically isolated, it is fused with a suitable myeloma cell line to obtain a hybridoma. This method can be carried out according to the method of Kohler and Milstein (Nature 256: 495-497, 1975).

The hybridoma cell line obtained by the above method may be cultured in a suitable culture liquid, and the hybridoma cell lines producing the antibodies that exhibit specific reactions to the present antigen are selected and cloned. For the cloning of the antibody-producing hybridomas, there may be employed the soft-agar method (Eur. J. Immunol. 6: 511-5198, 1976) in addition to the limit dilution method. The monoclonal antibodies thus produced are purified by such methods as column chromatography using protein A.

In addition to the above monoclonal antibodies, molecules used as a probe may be generated. For example, recombinant antibody has been described in detail in a review by Hoogenboon (Trends in Biotechnology, 15: 62-70, 1997).

Detection System Using a Probe

The monoclonal antibodies produced according to the present invention are used as test reagents for the detection and quatitation of HCV structural proteins in an enzyme-linked immunosorbent assay, an enzymeimmunoassay, an enzyme immunodot assay, a radioimmunoassay, an aggregation-based assay, or another well known immunoassay. When labeled antibodies are used for the detection, fluorescent compounds, chemiluminescent compounds, enzymes, chromogenic substances, and the like may be used as the labeled compounds.

For example, when a sandwich reaction system-based method is used to detect the virus antigen in a sample (serum), the diagnostic kit to be used comprises one or more monoclonal antibodies coated onto the solid support (for example, an inner wall of a microtiter well), one or more monoclonal antibodies or a fragment thereof bound to the labeled substance. Any combination of a monoclonal antibody immobilized onto the solid support and a labeled monoclonal antibody may be used, and the combinations that provide high sensitivity may be selected.

Solid supports that may be used include, for example, microtiter plates, test tubes, and capillaries made of polystyrene, polycarbonate, polypropylene, or polyvinyl, beads (latex beads, red blood cells, metal compounds etc.), membranes (liposome etc.), filters, and the like.

EFFECTS OF THE INVENTION

In accordance with the method of the present invention, virus antigens can be conveniently released from the virus particle in a state suitable for an immunoassay that effects detection using antibody as a probe. Furthermore, by treating a sample containing the virus particle in accordance with the present invention, a simple and sensitive detection and quantitation of virus antigens can be effected by an immunoassay in which the antigen is detected using antibody etc. as a probe. It is also possible to create a kit, an assay kit and a diagnostic reagent that determines the presence or absence of viruses and quantitates viruses in the sample using an immunoassay that employs the sample treating method of the present invention.

EXAMPLES

The following examples illustrate the present invention, but they should not be construed to limit the scope of the present invention.

Example 1

Expression and Purification of a HCV-Derived Polypeptide (A) Construction of an Expression Plasmid A plasmid corresponding to the core region of HCV was constructed as follows: one microgram each of DNA of plasmids pUC.C11-C21 and pUC.C10-E12 obtained by integrating the C11-C21 clone and the C10-E12 clone (Japanese Unexamined Patent Publication (Kokai) No. 6 (1994)-38765) respectively, into pUC119 was digested in 20 µl of a restriction enzyme reaction solution [50 mM Tris-HCl, pH 7.5, 10 mM MgCl$_2$, 1 mM dithiothreitol, 100 mM NaCl, 15 units of EcoRI and 15 units of ClaI enzyme] and the restriction enzyme reaction solution [10 mM Tris-HCl, pH 7.5, 10 mM MgCl$_2$, 1 mM dithiothreitol, 50 mM NaCl, 15 units of ClaI and 15 units of KpnI enzyme] at 37° C. for one hour each, and then was subjected to 0.8% agarose gel electrophoresis to purify about 380 bp of EcoRI-ClaI fragment and about 920 bp of ClaI-KpnI fragment.

To the two DNA fragments and a vector obtained by digesting pUC119 with EcoRI and KpnI was added to 5 µl of 10× ligase buffer solution [660 mM Tris-HCl, pH 7.5, 66 mM MgCl$_2$, 100 mM dithiothreitol, 1 mM ATP], 1 µl of T4 lgase (350 units/µl) and water to make total volume 50 µl, and then was incubated at 16° C. overnight to carry out a ligation reaction. Using this plasmid, E. coli JM109 was transformed to obtain the plasmid pUC.C21-E12.

One nanogram of the DNA of this plasmid, pUC.C21-E12, was subjected to PCR using two primers: 5'-GAAT-TCATGGGCACGAATCCTAAA-3' (SEQ ID NO: 7), and 5'-TTAGTCCTCCAGAACCCGGAC-3' (SEQ ID NO: 8). PCR was carried out using the GeneAmp™ (DNA Amplification Reagent Kit, manufactured by Perkin Elmer Cetus) under the condition of DNA denaturation at 95° C. for 1.5 min, annealing at 50° C. for 2 min, and DNA synthesis at 70° C. for 3 min. DNA fragments thus obtained were separated on 0.8% agarose gel electrophoresis and were purified by the glass powder method (Gene Clean).

On the other hand, pUC19 was digested with SmaI, and the DNA fragment obtained by PCR was added to 5 µl of 10× ligase buffer solution [660 mM Tris-HCl, pH 7.5, 66 mM MgCl$_2$, 100 mM dithiothreitol, 1 mM ATP], 1 µl of T4 lgase (350 units/µl) and water to make total volume 50 µl, and then were incubated at 16° C. overnight to carry out a ligation reaction. Using this plasmid, E. coli JM109 was transformed to obtain the plasmid pUC.C21-E12.SmaI. One microgram of this plasmid DNA was digested in 20 µl of the restriction enzyme reaction solution [150 mM NaCl, 6 mM Tris-HCl, pH 7.5, 6 mM MgCl$_2$, 15 units of EcoRI and 15 units of BamHI enzyme] and then was subjected to 0.8% agarose gel electrophoresis to separate about 490 bp of EcoRI-BamHI fragment, which was purified by the glass powder method.

Then 1 µg of the DNA of the expression vector Trp.TrpE (Japanese Unexamined Patent Publication (Kokai) No. 5 (1993)-84085) was digested in 20 µl of the restriction enzyme reaction solution [150 mM NaCl, 6 mM Tris-HCl, pH 7.5, 6 mM MgCl$_2$, 15 units of EcoRI and 15 units of BamHI enzyme] at 37° C. for 1 hour. To the reaction mixture was added 39 µl of water and then was heated at 70° C. for 5 minutes. Thereafter 1 µl of a bacterial alkaline phosphatase (BAP) was added and incubated at 37° C. for 1 hour.

Phenol was added to the reaction mixture for phenol extraction. The aqueous layer thus obtained was precipitated with ethanol and the precipitate obtained was dried. One microgram of DNA of the EcoRI-BamHI-treated vector obtained and the above core 140 fragment were added to 5 µl of 10× ligase buffer solution [660 mM Tris-HCl, pH 7.5, 66 mM MgCl$_2$, 100 mM dithiothreitol, 1 mM ATP], 1 µl of T4 lgase (350 units/µl) and water to make total volume 50 µl, and were incubated overnight at 16° C. to carry out a ligation reaction.

Using 10 µl of this reaction mixture, E. coli strain HB101 was transformed. The sensitive E. coli strain used for transformation can be constructed by the calcium chloride method [Mandel, M. and Higa, A., J. Mol. Biol., 53, 159-162 (1970)]. The transformed E. coli was plated on a LB plate (1% tryptophan, 0.5% NaCl, 1.5% agar) containing 25 µg/ml ampiciliin and was incubated overnight at 37° C. Using an inoculating loop, one loopful of a the bacterial colony that has formed on the plate was transferred to an LB culture medium containing 25 µg/ml ampicillin and incubated overnight at 37° C. One and a half milliliters of the bacterial culture was centrifuged to collect the cells and then the plasmid DNA was subjected to minipreparation using the alkali method [Manniatis et al., Molecular Cloning: A Laboratory Manual (1982)].

Then 1 µg of the DNA of the plasmid DNA thus obtained was digested in 20 µl of the restriction enzyme reaction solution [150 mM NaCl, 6 mM Tris-HCl, pH 7.5, 6 mM MgCl$_2$, 15 units of EcoRI and 15 units of BamHI enzyme] at 37° C. for 1 hour, and then was subjected to agarose gel electrophoresis. The Trp.TrpE core 160 expression plasmid that produced about 490 bp of EcoRI-BamHI fragment were selected.

(B) Expression and Purification of a Polypeptide Encoded by the Clone Core 160

E. coli strain HB101 having an expression plasmid Trp-.TrpE core 160 was inoculated to 3 ml of 2YT medium (1.6% trypton, 1% yeast extracts, 0.5% NaCl) containing 50 µg/ml of ampicillin, and was cultivated at 37° C. for 9 hours. One milliliter of the culture was passaged to 100 ml of M9-CA medium (0.6% Na$_2$HPO$_4$, 0.5% KH$_2$PO$_4$, 0.5% NaCl, 0.1% NH$_4$Cl, 0.1 mM CaCl$_2$, 2 mM MgSO$_4$, 0.5% casamino acid, 0.2% glucose) containing 50 µg/ml of ampicillin, and cultured at 37° C. Indol acrylate was added to a final concentration of 40 mg/l at OD600=0.3 and was cultured for more 16 hours. The culture was centrifuged to collect the cells.

To the cells was added 20 ml of the buffer A [50 mM Tris-HCl, pH 8.0, 1 mM EDTA, 30 mM NaCl] to suspend them. The suspension was again centrifuged to obtain 2.6 g of expression cells. The cells thus obtained were suspended in 10 ml of the buffer A. After disrupting the membrane of the E. coli with sonication, it was centrifuged to obtain an insoluble fraction containing a fusion polypeptide of a polypeptide encoded by HCV cDNA and TrpE. To the fraction was added 10 ml of the buffer A containing 6 M urea to solubilize and extract the fusion polypeptide. The solubilized extract was subjected to ion exchange column chromatography using S-Sepharose to purify the fusion polypeptide.

Example 2

Method of Constructing a Hybridoma

The fusion polypeptide (TrpC11) prepared by the method described above was dissolved in 6 M urea, and then diluted in 10 mM phosphate buffer, pH 7.3, containing 0.15 M NaCl to a final concentration of 0.2 to 1.0 mg/ml, and mixed with an equal amount of adjuvant (Titermax) to make a TrpC11 suspension. This suspension prepared at 0.1 to 0.5 mg/ml of TrpC11 was intraperitoneally given to 4 to 6 week old BALB/c mice. Similar immunization was conducted every two weeks and after about two more weeks 10 µg of TrpC11 dissolved in physiological saline was administered through the tail vein.

Three days after the last booster, the spleen was aseptically isolated from the immunized animal and was cut into pieces using scissors, which were then crumbed into individual cells and washed three times with the RPMI-1640 medium. After washing, a mouse myeloma cell line SP2/0Ag14 at the logarithmic growth phase as described above, $2.56 \times 10^7$ of said cells and $1.64 \times 10^8$ spleen cells were mixed in a 50 ml centrifuge tube. The mixture was centrifuged at 200×g for 5 minutes, the supernatant was removed, and 1 ml of the RPMI-1640 medium containing 50% polyethylene glycol (PEG) 4000 (manufactured by Merck) was added to the precipitate, and 10 ml of the RPMI-1640 medium was further added to carry out cell fusion.

After PEG was removed by centrifugation (200×g, 5 minutes), the fused cells were cultured in a RPMI1640 medium containing 10% bovine serum, hypoxanthine, aminopterin, and thymidine (hereinafter referred to as HAT) in a 96-well plate for about 10 days to grow only hybridomas. Then, the clones producing the antibody of interest were detected by the ELISA method to obtain the hybridomas that produce monoclonal antibody having the desired reaction specificity of the present invention.

The hybridomas thus obtained were monocloned according to the conventional limiting dilution method, and the hybrodomas obtained were designated HC11-11, HC11-14, HC11-10, and HC11-3, and HC11-7. Said four hybridomas were deposited with the National Institute of Bioscience and Human Technology, Agency of Industrial Science and Technology, on Jul. 4, 1997, as FERM BP-6005, FERM BP-6006, FERM BP-6004, FERM BP-6002, AND FERM BP-6003, respectively.

Example 3

Construction of Monoclonal Antibody

The hybridomas obtained in the method of Example 2 were inoculated to the abdominal cavity of mice treated with pristane etc., and the monoclonal antibodies produced in the ascites fluid was collected. The monoclonal antibodies were purified using the Protein A-bound Sepharose column to separate IgG fractions.

By an immunoassay using rabbit anti-mouse Ig isotype antibody (manufactured by Zymed), the isotype of each of the monoclonal antibodies C11-14, C11-11, C11-10, C11-7, and C11-3 produced from the above five hybridomas, respectively, was found to be IgG2 for C11-10 and C11-7; and IgG1 for CH11-11, C11-14, and C11-3. For the five monoclonal antibodies obtained, epitope analysis was conducted using the synthetic peptides composed of 20 amino acids synthesized according to the sequence derived from the HCV core region. The result indicated, as shown in Table 1, that they were the monoclonal antibodies that specifically recognize part of the core region.

TABLE 1

| Antibody | Recognition site |
|---|---|
| C11-14 | $^{41}$Gly-$^{50}$Arg (SEQ ID NO: 4) |
| C11-10 | $^{21}$Asp-$^{40}$Arg (SEQ ID NO: 3) |
| C11-3 | $^{100}$Pro-$^{120}$Gly (SEQ ID NO: 5) |
| C11-7 | $^{111}$Asp-$^{130}$Phe (SEQ ID NO: 6) |
| C11-11 | $^{100}$Pro-$^{120}$Gly (SEQ ID NO: 5) |

Example 4

Study on the Condition of Sample Treatment

1) SDS Concentration

To 100 µl of a normal human serum and HCV-RNA-positive sera were added 100 µl of the treatment solution containing a different concentration of SDS and 0.6% CHAPS. The mixtures were then placed in an incubator set at 56° C. and were treated for 30 minutes, and 80 µl each of the treated mixtures was used as a sample. The result obtained using the assay method described below is shown in FIG. 1 with the SDS concentration at the time of treatment taken as the abscissa.

2) CHAPS Concentration

Figure 2:
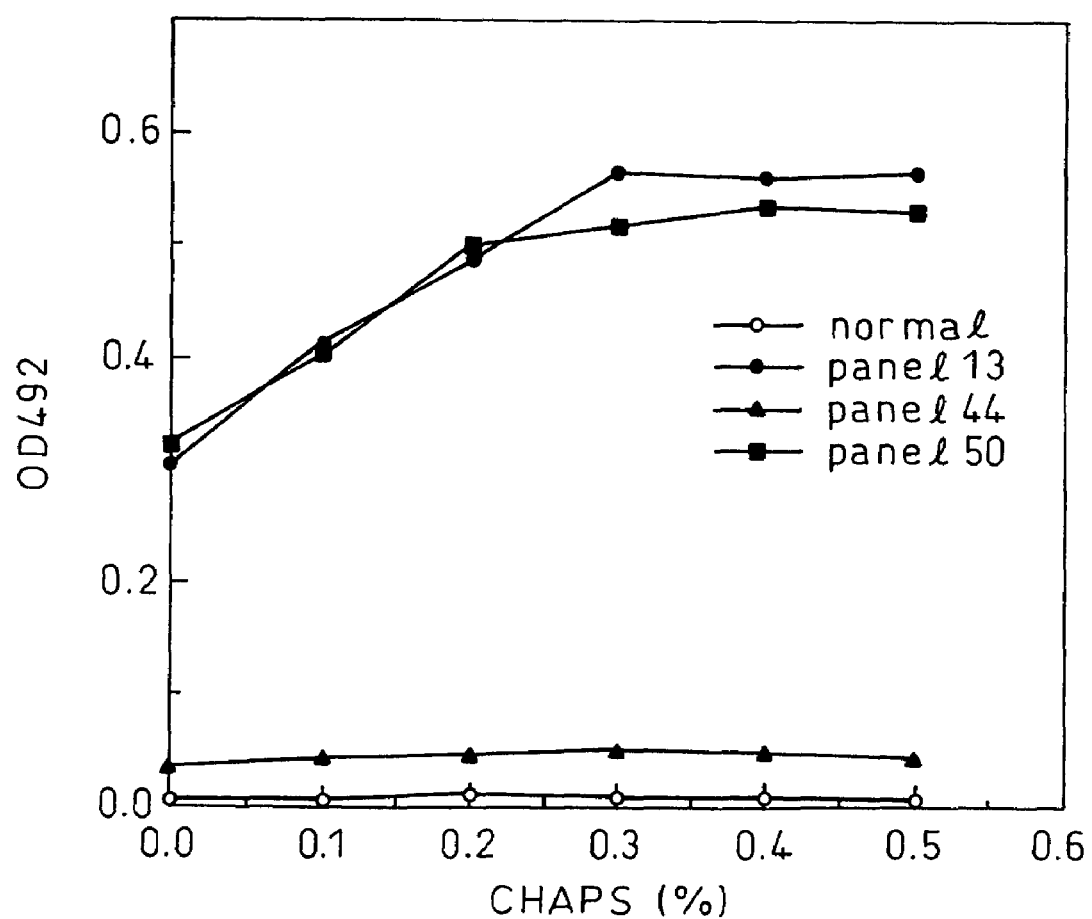
FIG. 2 is a graph showing the effect of concentration of added CHAMPS on sample treatment. Sera from normal healthy human subjects (normal) and HCV-RNA-positive panel sera 13 and 50 were used.

To 100 µl of a normal human serum and HCV-RNA-positive sera were added 100 µl of the treatment solution containing a different concentration of CHAPS and 5% SDS. The mixtures were then placed in an incubator set at 56° C. and were treated for 30 minutes, and 80 µl each of the treated mixtures was used as a sample. The result obtained using the assay method described below is shown in FIG. 2 with the CHAPS concentration at the time of treatment taken as the abscissa.

3) Urea Concentration

Figure 3:
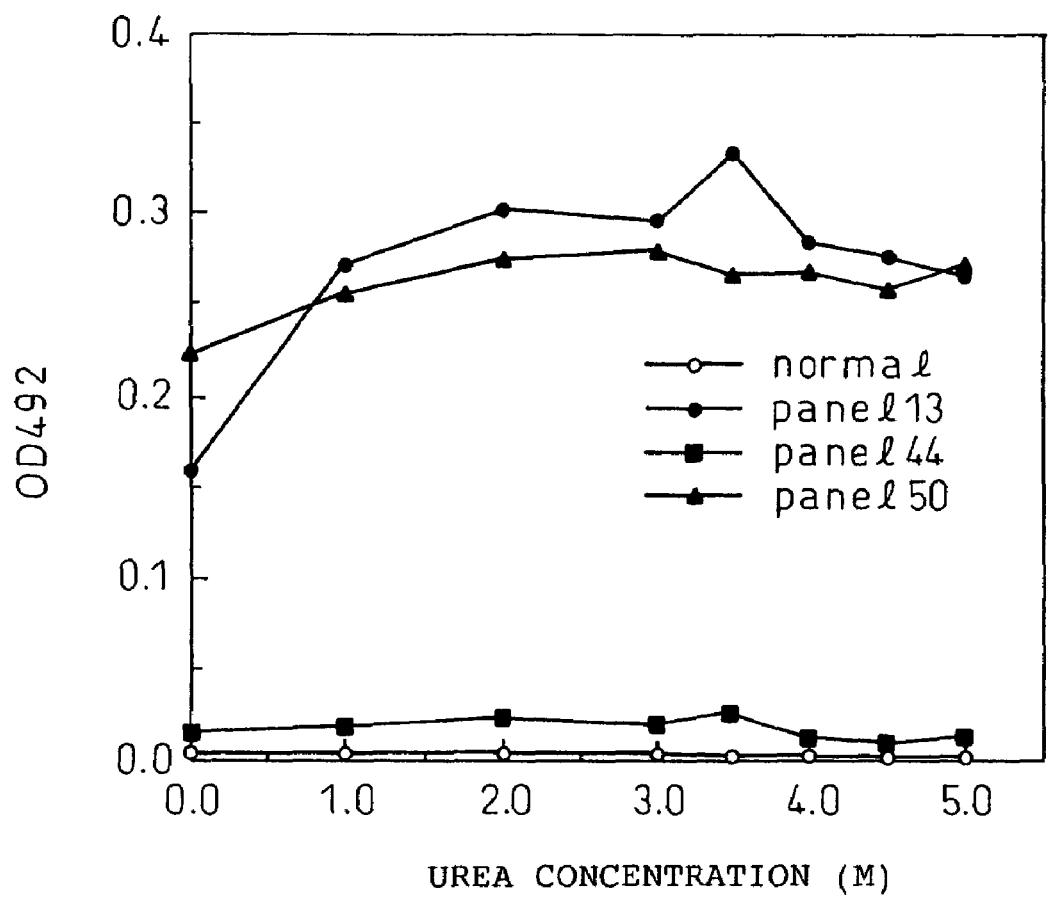
FIG. 3 is a graph showing the effect of concentration of added urea on sample treatment. Sera from normal healthy human subjects (normal) and HCV-RNA-positive panel sera 13, 44, and 50 were used.

To 100 µl of a normal human serum and HCV-RNA-positive sera were added 100 µl of the treatment solution (5% SDS, 0.6% CHAPS) containing a different concentration of urea. The mixtures were then placed in an incubator set at 56° C. and were treated for 30 minutes, and 80 µl each of the treated mixtures was used as a sample. The result obtained using the assay method described below is shown in FIG. 3 with the urea concentration at the time of treatment taken as the abscissa.

4) Triton X100 Concentration

Figure 4:
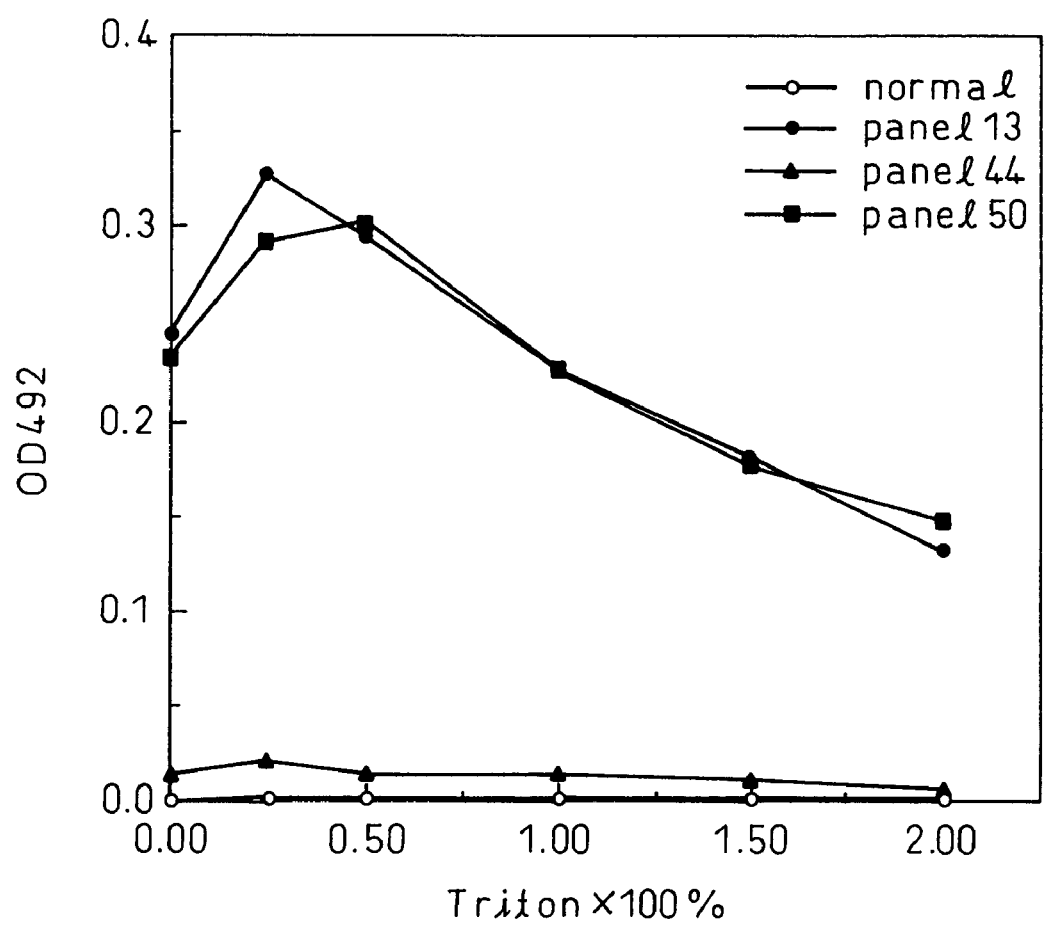
FIG. 4 is a graph showing the effect of temperature of added Triton X100 on sample treatment. Sera from normal healthy human subjects (normal) and HCV-RNA-positive panel sera 13, 44, and 50 were used.

To 100 µl of a normal human serum and HCV-RNA-positive sera were added 100 µl of the treatment solution (5% SDS, 0.6% CHAPS, 6 M urea) containing a different concentration of Triton X100. The mixtures were then placed in an incubator set at 56° C. and were treated for 30 minutes, and 80 µl each of the treated mixtures was used as a sample. The result obtained using the assay method described below is shown in FIG. 4 with the Triton X100 concentration at the time of treatment taken as the abscissa.

5) Reaction Temperature

Figure 5:
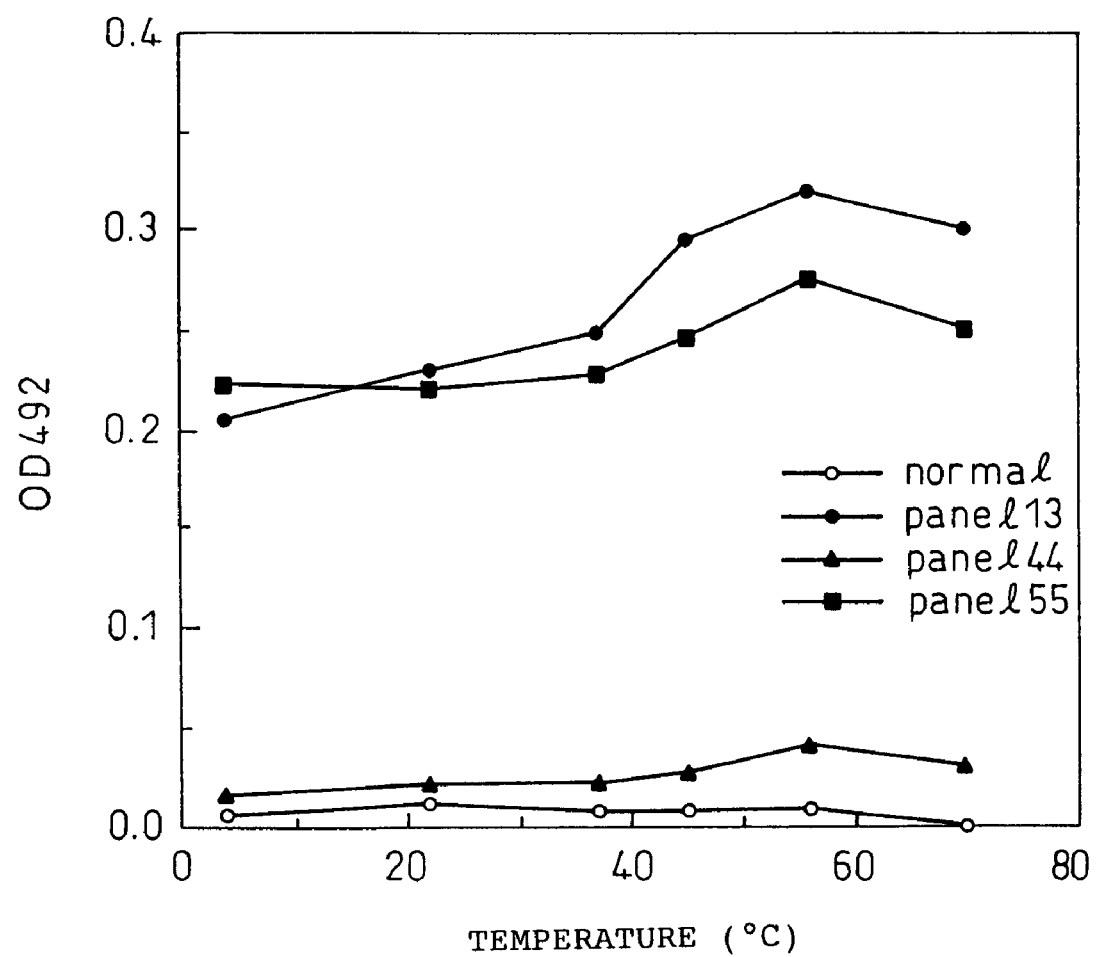
FIG. 5 is a graph showing the effect of temperature during sample treatment. Sera from normal healthy human subjects (normal) and HCV-RNA-positive panel sera 13, 44, and 50 were used.

To 100 μl of a normal human serum and HCV-RNA-positive sera were added 100 μl of the treatment solution (5% SDS, 0.6% CHAPS, 6 M urea, 0.75% Triton X100). The mixtures were treated at 4° C., room temperature (23° C.), 37° C., 45° C., 56° C., and 70° C. for 30 minutes, and 80 μl each of the treated mixtures were used as a sample. The result obtained using the assay method described below is shown in FIG. 5.

Assay Methods

Samples obtained in the study on the condition of serum treatment were each evaluated using the respective assay method described below. Thus, an anti-HCV core antigen monoclonal antibody (a mixture of equal amounts of antibody C11-3 and C11-7) was diluted to a final total concentration of 6 μg/ml in 0.1 M carbonate buffer, pH 9.6, and 100 μl each of the dilutions was dispensed per well of a 96-well microtiter plate (manufactured by Nunc). After the plate was incubated overnight at 4° C., it was washed twice with 0.35 ml of 10 mM sodium phosphate buffer, pH 7.3, containing 0.15 M NaCl. Then, 0.35 ml of 10 mM sodium phosphate buffer, pH 7.35, containing 0.5% casein-Na (hereinafter referred to as the blocking solution) was added and the plate was further incubated at room temperature for 2 hours.

After the blocking solution was removed, 160 μl of 100 mM sodium phosphate buffer, pH 7.3, containing 0.15 M NaCl, 1% BSA, 0.5% casein-Na, and 0.05% Tween 20, and samples for measurement obtained by the serum treating method were added into respective wells. The plate was then incubated at room temperature for 2 hours, washed five times with 300 μl of the wash solution. Then 100 μl of a peroxidase (POD)-labeled monoclonal antibody (a mixture of equal amounts of C11-10 and C11-14) was added and was incubated at room temperature for 30 minutes. After the incubation was over, the plate was washed five times with 300 μl of the above wash solution. One hundred microliters of the substrate (ortho-phenylene diamine, hereinafter referred to as OPD) solution was added to the plate and the plate was incubated at room temperature for 30 minutes, followed by the addition of 100 μl of 2 N sulfuric acid solution. Absorbance was measured at a wavelength of 492 nm (OD492) with the absorbance at 630 nm as a reference.

Each treatment condition was optimized, as shown in FIGS. 1 to 4. It was difficult to detect the core antigen in the untreated samples, but such a simple treatment enabled the detection of the core antigen. Especially, it was shown, the core antigen can be satisfactorily detected by employing the condition of SDS at 0.5% or greater, CHAPS at 0.1% or greater, urea at 1M or greater, and Triton X100 at 0.1 to 0.75%, and a temperature range of 4° C. to 70° C.

Example 5

The Detection and Assay Method of the Core Antigen in the Structural Region (1)

To 100 μl of serum was added 100 μl of the treatment solution (5% SDS, 0.6% CHAPS, 6 M urea, 0.75% Triton X100). It was then placed in an incubator set at 56° C. and was treated for 30 minutes, and 120 μl of the treated mixture was used as a sample.

An anti-HCV core antigen monoclonal antibody (a mixture of equal amounts of C11-3 and C11-7) was diluted to a final total concentration of 6 μg/ml in 0.1 M carbonate buffer, pH 9.6, and 100 μl each of the diluted mixture was dispensed per well of a 96-well microtiter plate (manufactured by Nunc). After the plate was incubated overnight at 4° C., it was washed twice with 0.35 ml of 10 nM sodium phosphate buffer, pH 7.3, containing 0.15 M NaCl. Then, 0.35 ml of the blocking solution was added and the plate was further incubated at room temperature for 2 hours.

After the blocking solution was removed, 120 μl of the reaction buffer and samples for measurement obtained in the above treating method were added into respective wells, and incubated at room temperature for 2 hours. The plate was washed five times with 300 μl of the wash solution, and then 100 μl of a peroxidase (POD)-labeled monoclonal antibody (a mixture of equal amounts of C11-10 and C11-14) was added to the plate and the plate was incubated at room temperature for 30 minutes. The plate was washed five times with 300 μl of the wash solution and 100 μl of the substrate (OPD) solution was added, and incubated at room temperature for 45 minutes, followed by the addition of 100 μl of 2 N sulfuric acid solution. Absorbance was measured at a wavelength of 492 nm (OD492) with the absorbance at 630 nm as a reference. As a standard serum, the panel serum 50, defined as 1 U/ml, was serially diluted in 10 mM sodium phosphate buffer, pH 7.3, containing 1% BSA, which was similarly treated and measured.

Figure 6:
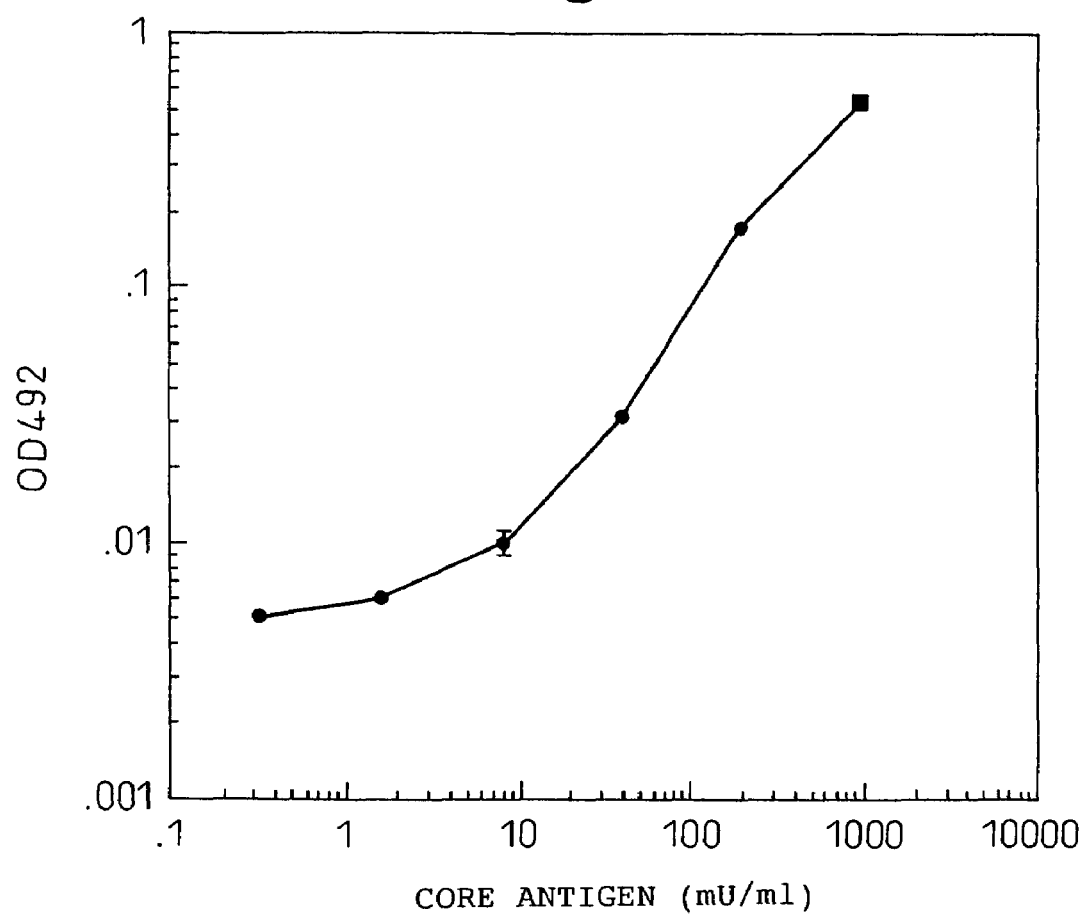
FIG. 6 is a graph showing the dilution standard curve and the detection limit of a sandwich assay system in which a standard panel serum 50, defined as 1 U/ml, was serially diluted and subjected to a sample treating method, and then was measured using a monoclonal antibody of the present invention.

FIG. 6 shows a dilution line of the panel serum 50 used as a standard serum. The core antigen in the sample was determined in a dose-dependent manner and could be detected to a level of about 0.5 mU/ml. It was demonstrated, therefore, that by combining a very simple method of sample treatment and the monoclonal antibody of the present invention, the HCV core antigen can be detected or quantitated.

Example 6

Detection and Quantitation of the HCV Core Antigen (2)

A Method Using an Alkaline Phosphatase-Labeled Monoclonal Antibody

Figure 7:
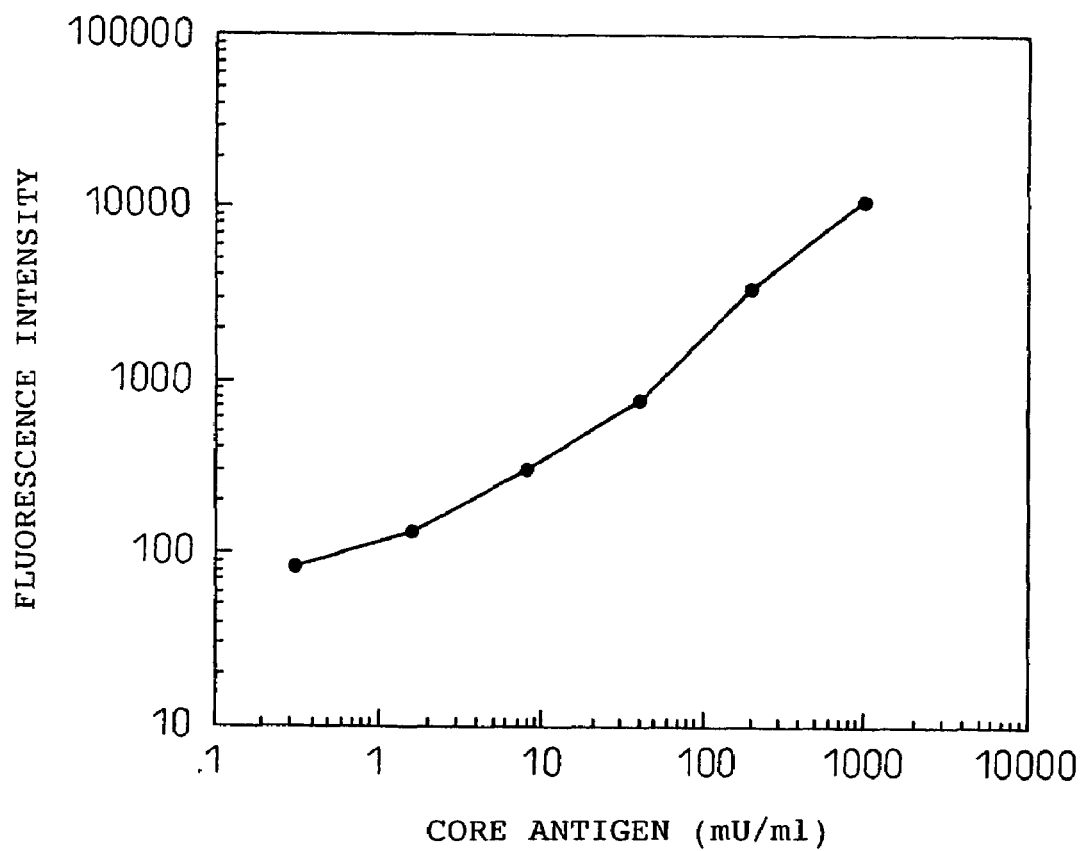
FIG. 7 is a graph showing the dilution standard curve and the detection limit of a sandwich immunoassay system in which a standard panel serum 50, defined as 1 U/ml, was serially diluted and subjected to a sample treating method, and then was measured.
Figure 8:
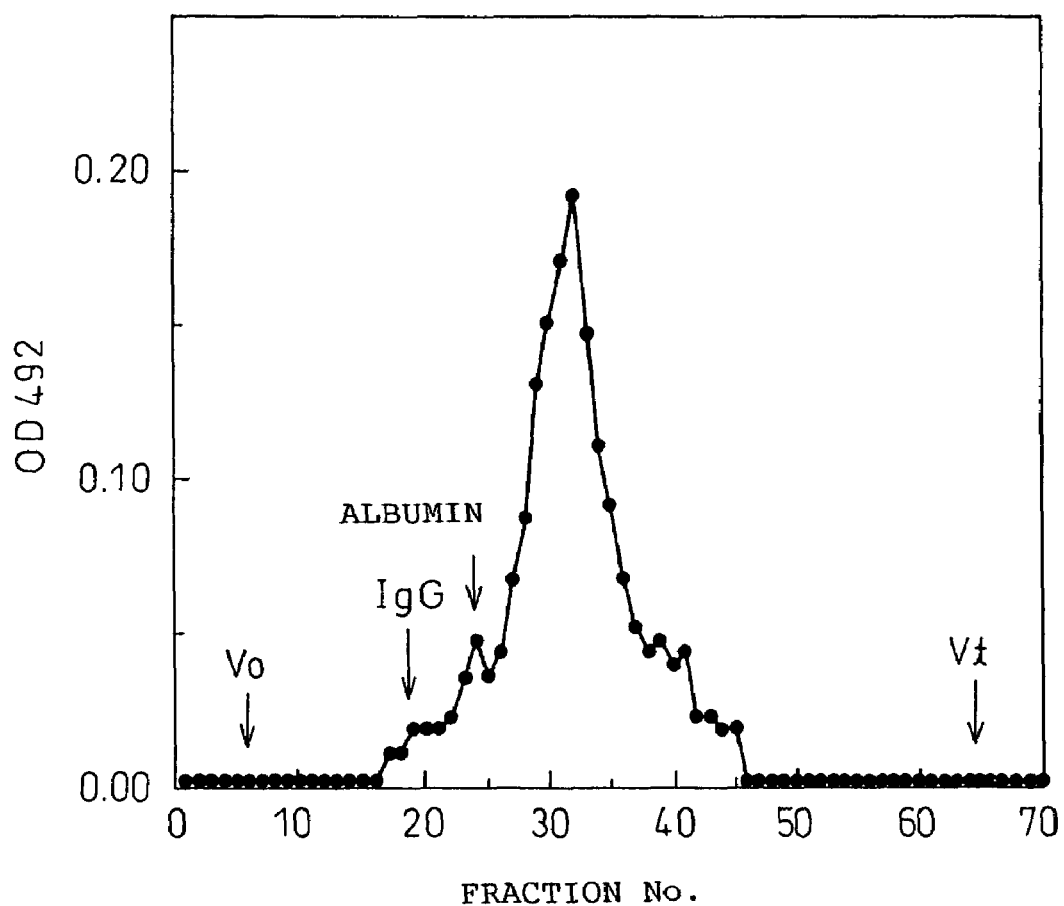
FIG. 8 shows an immunological activity of core antigen in fractions obtained by fractionation with a gel filtration column of the panel serum 13 that was subjected to sample treating method. The molecular weight is about 150 kD and about 68 kD for IgG and albumin, respectively.

A 96-well black microtiter plate (Nunc) as the solid carrier, an alkaline phosphatase-labeled monoclonal antibody as the labeled antibody, and CDPstar (Emerald II as the sensitizer) as the substrate were used. A dilution line of the panel serum 50 used as a standard serum is shown in FIG. 7, in which the core antigen in the sample was determined in a dose-dependent manner and could be detected to a level of about 0.5 mU/ml. It was demonstrated, therefore, that the method using an alkaline phosphatase-labeled monoclonal antibody can also detect or quantitate the HCV core antigen.

Example 7

Study on Additives for Suppressing Sensitivity Reduction in the Hemolyzed Serum

When serum components were tested on the effect on sensitivity, it was found that the addition of hemoglobin drastically reduced sensitivity. It was thought that the reduction was caused by the heme released from the denatured hemoglobin produced by pretreatment using a pretreatment agent containing SDS, CHAPS, or Triton X100. Thus, additives that could reduce the effect of the denatured hemoglobin were tested by adding them to the pretreatment agent.

The effect of urea addition was studied by adding urea to the model samples that were created by adding a high concentration hemoglobin (manufactured by Kokusai Shiyaku: Kansho Check) to a HCV core antigen positive serum (panel serum No. 3), and by determining the core antigen according to Example 6. The level of activity of the core antigen in the 430 mg/dl hemoglobin addition group relative to 100% of the no-hemoglobin addition group used as the control is shown in Table 2. It was confirmed that when no urea is added, the level of activity of the core antigen in the hemoglobin addition group decreased by 30%, but by increasing the amount of added urea the level of activity of the core antigen in the hemoglobin addition group increased and interference by hemoglobin decreased.

TABLE 2

Suppressive effect of urea on interference by hemoglobin

| Additive | % Relative to control |
|---|---|
| No addition | 30.0 |
| 0.5 M urea | 36.3 |
| 1 M urea | 39.7 |
| 2 M urea | 43.0 |
| 3 M urea | 48.8 |
| 4 M urea | 53.7 |

On the other hand, since there is a possibility of the interaction of each of amino acids with the heme and the buffering effect by the amino group and the carboxyl group, various amino acids were added and the degree of the effect was examined. The result is shown in Table 3.

TABLE 3

Suppressive effect of various amino acids on interference by hemoglobin

| Additive | % Relative to control |
|---|---|
| No addition | 22.7 |
| 0.1 M histidine | 53.7 |
| 0.1 M tryptophan | 70.8 |
| 0.1 M phenylalanine | 45.8 |
| 0.1 M leucine | 25.9 |
| 0.1 M glutamine | 36.1 |
| 0.1 M lysine | 42.1 |
| 0.1 M arginine | 31.4 |
| 0.1 M glutamic acid | 49.8 |
| 0.1 M glycine | 39.1 |
| 0.1 M proline | 31.2 |
| 0.1 M serine | 32.5 |

Tryptophan and histidine exhibited the most potent suppressive effect on interference. The dose-dependency of the suppressive effect on interference was studied and the result is shown in Table 4.

TABLE 4

Suppressive effect of histidine and tryptophan on interference by hemoglobin

| Additive | % Relative to control |
|---|---|
| No addition | 24.2 |
| 0.05 M histidine | 49.3 |
| 0.1 M histidine | 59.4 |
| 0.15 M histidine | 74.5 |
| 0.2 M histidine | 77.0 |
| 0.05 M tryptophan | 58.7 |
| 0.1 M tryptophan | 71.5 |
| 0.15 M tryptophan | 77.9 |
| 0.2 M tryptophan | 89.0 |

Since the heme is coordinated by a side chain in hemoglobin and retained in hemoglobin, the effect was suggested to be attributable to the side chain. Accordingly, the effect of imidazole, a side chain in histidine, and indoleacrylic acid containing an indole ring, a side chain in tryptophan, were studied and the result is shown in Table 5.

TABLE 5

Suppressive effect of imidazole and indoleacrylic acid on interference by hemoglobin

| Additive | % Relative to control |
|---|---|
| No addition | 22.1 |
| 0.05 M imidazole | 35.2 |
| 0.1 M imidazole | 42.0 |
| 0.15 M imidazole | 58.8 |
| 0.2 M imidazole | 70.7 |
| 5 mM indoleacrylic acid | 50.4 |
| 10 mM indoleacrylic acid | 69.0 |
| 20 mM indoleacrylic acid | 90.3 |
| 30 mM indoleacrylic acid | 96.8 |

When indole or indoleacrylic acid was added to the reaction, a dose-dependent suppressive effect of interference by hemoglobin was observed as with the addition of amino acids. This indicated that by adding to the reaction a substance that contains an imidazole ring, for example histidine, or an indole ring, for example tryptophan, the sensitive detection of the core antigen can be attained even for the samples that contains hemoglobin.

The effect of combination of the above additives was studied. The result is shown in Table 8. By combining histidine and tryptophan, recovery of 90% or greater was obtained, and the addition of urea further increased detection sensitivity.

TABLE 6

| Additive | % Relative to control |
|---|---|
| 0.1 M histidine/0.1 M tryptophan | 91.1 |
| 4 M urea/0.1 M Tris/0.1 M histidine | 112.6 |

Example 8

Analysis the Molecular Form Recognized in the Serum Treatment and in the Assay Method Each method of serum treatment was used to treat 0.25 ml of the panel serum 13. The treated serum was fractionated on a gel filtration column (Superdex 200HR, 1×30), and anti-core immunological activity in the fractions was measured. The result is shown in Table 8. The figure suggested that the molecules having a molecular weight of about 20 to 30 kDa are being recognized and that the core antigen in the virus has been released through the disruption of the virus and the inactivation of the anti-core antibody in the serum by the above-mentioned pretreatment.

Example 9

Assay Method of the Core Antigen in the HCV Structural Region in the Serum

Sera determined to have $10^3$ to $10^7$ copies/ml of HCV-RNA using AmpliCore HCV Monitor kit (Roche), a PCR method, and normal human sera were used to quantitate the HCV core antigen in the sera using the method described above.

Figure 9:
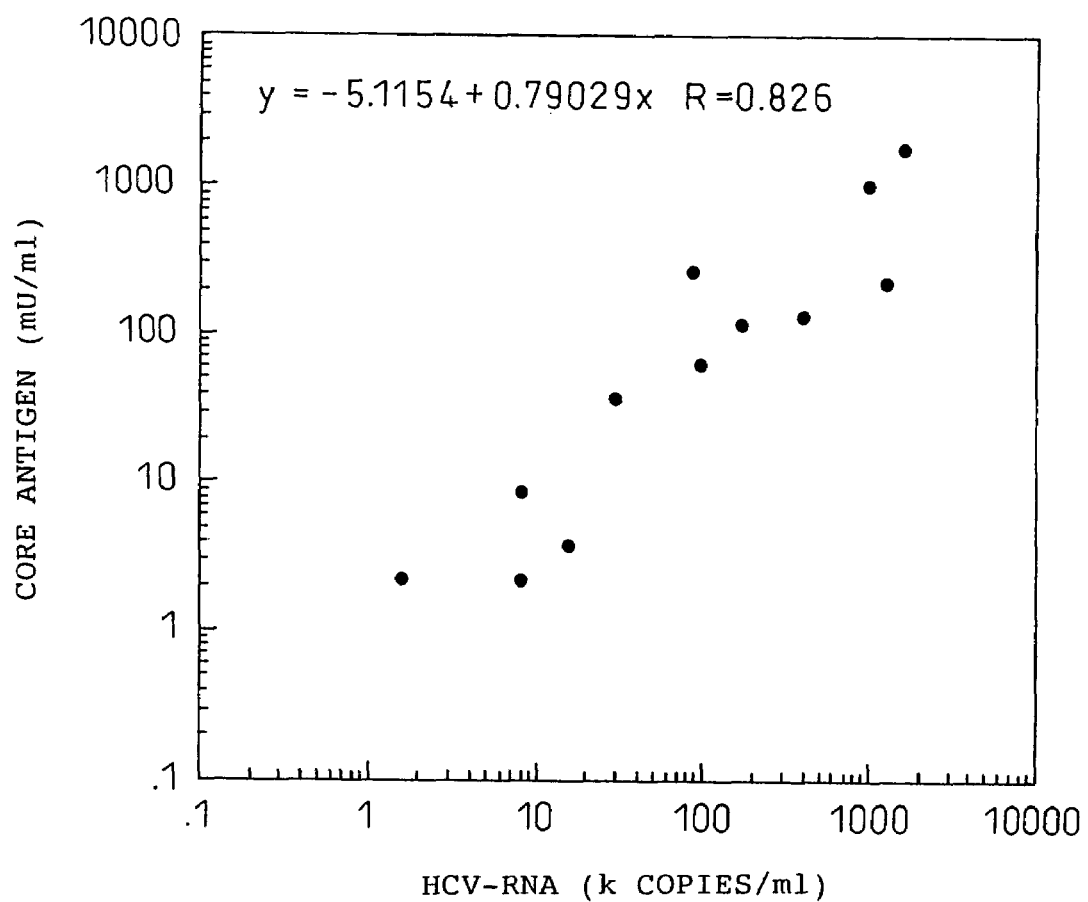
FIG. 9 is a graph showing a correlation between the activity of core antigen released and the amount of HCV-RNA determined using Amplicore HCV Monitor (PCR method) of a PCR-positive sample which was subjected to a sample treating method of the present invention.

As a standard serum the panel serum 50 (defined as 1 U/ml) was serially diluted in 10 mM sodium phosphate buffer, pH 7.3, containing 1% BSA, and treated in a similar manner. The result is shown in Table 7. Of the samples tested, the core antigen in all the normal human sera was below the detection limit and could be detected in all of the PCR-positive samples. The correlation is shown in FIG. 9, which revealed that the correlation with the PCR method was also as high as 0.8 or greater.

TABLE 7

Levels of HCV-RNA and the core antigen

| Sample # | | RNA (K copies/ml) | core antigen (mU/ml) |
|---|---|---|---|
| Normal human serum | 1 | — | N.D. |
| | 2 | — | N.D. |
| | 3 | — | N.D. |
| | 4 | — | N.D. |
| | 5 | — | N.D. |
| Panel serum | 81 | 1.6 | 2.1 |
| | 80 | 8 | 2.1 |
| | 82 | 8 | 8.5 |
| | 33 | 16 | 3.7 |
| | 31 | 30 | 37.0 |
| | 26 | 87 | 266.7 |
| | 39 | 97 | 63.8 |
| | 41 | 170 | 116.1 |
| | 16 | 400 | 133.7 |
| | 50 | 1000 | 1000 |
| | 45 | 1300 | 277.3 |
| | 13 | 1600 | 1806 |

N.D.: Not detected

Example 10

Study on the Condition of Sample Treatment Study on Treatment Conditions

1) Guanidine Hydrochloride Concentration

Figure 10:
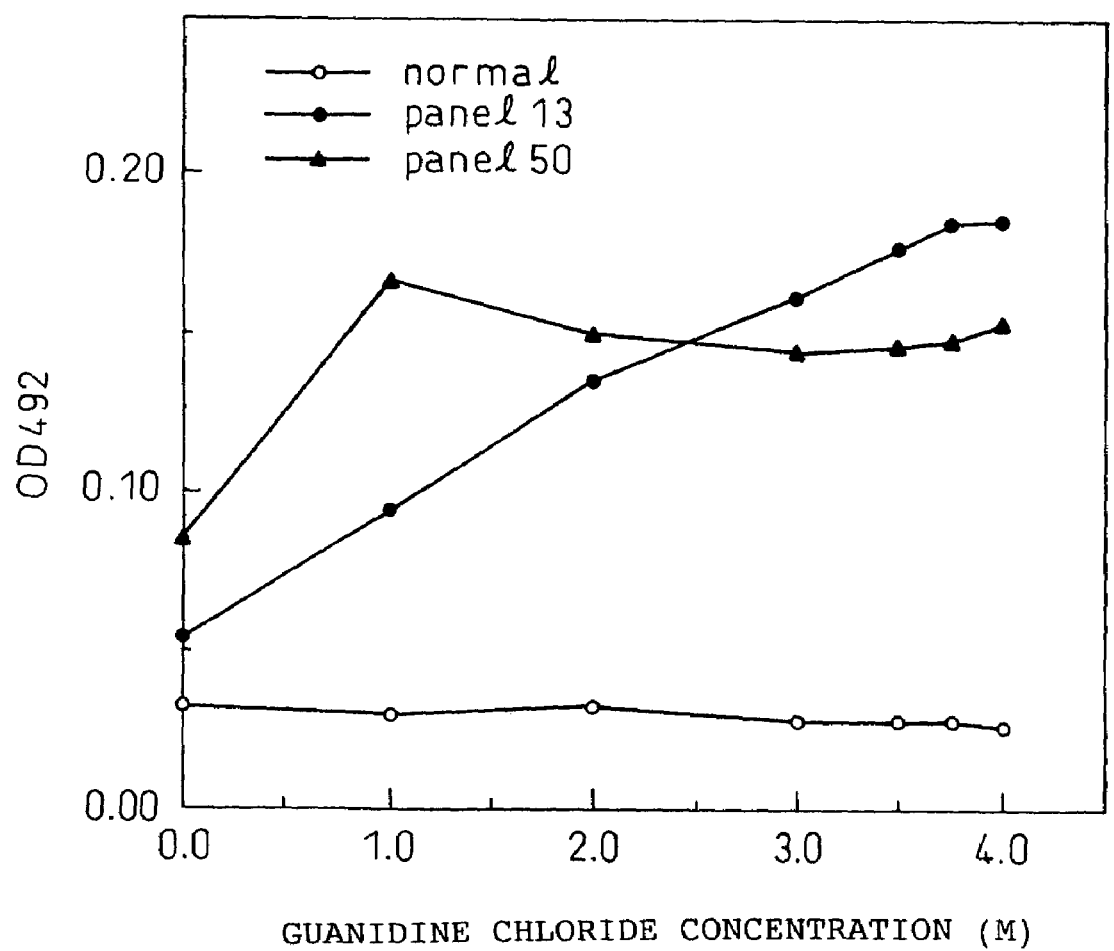
FIG. 10 is a graph showing the effect of concentration of added guanidine chloride on sample treatment. Sera from normal healthy human subjects (normal) and HCV-RNA-positive panel sera 13 and 50 were used.

To 100 μl of a normal human serum and HCV-RNA-positive sera were added 100 μl of the treatment solution containing a different concentration of guanidine hydrochloride and 0.5 N HCl. The mixtures were treated at room temperature for 30 minutes, and 80 μl each of the treated mixtures was used as a sample. The result obtained using the assay method described below is shown in FIG. 10 with the guanidine hydrochloride concentration at the time of treatment taken as the abscissa.

2) Triton X100 Concentration

Figure 11:
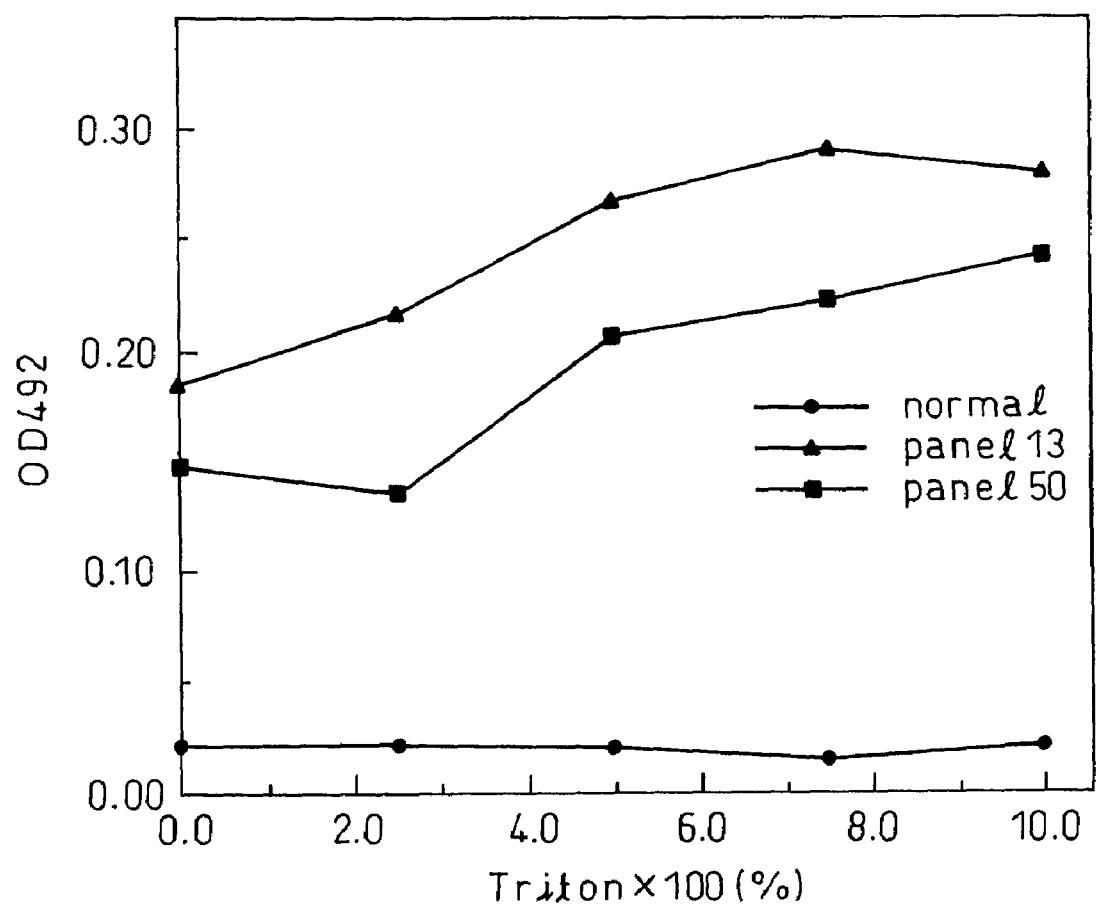
FIG. 11 is a graph showing the effect of concentration of added Triton X100 on sample treatment. Sera from normal healthy human subjects (normal) and HCV-RNA-positive panel sera 13 and 50 were used.

To 100 μl of a normal human serum and HCV-RNA-positive sera were added 100 μl of the treatment solution containing a different concentration of Triton X100 (6 M guanidine hydrochloride, 0.5 N HCl). The mixtures were treated at room temperature for 30 minutes, and 80 μl each of the treated mixtures was used as a sample. The result obtained using the assay method described below is shown in FIG. 11 with the Triton X100 concentration at the time of treatment taken as the abscissa.

3) Tween 20 Concentration

Figure 12:
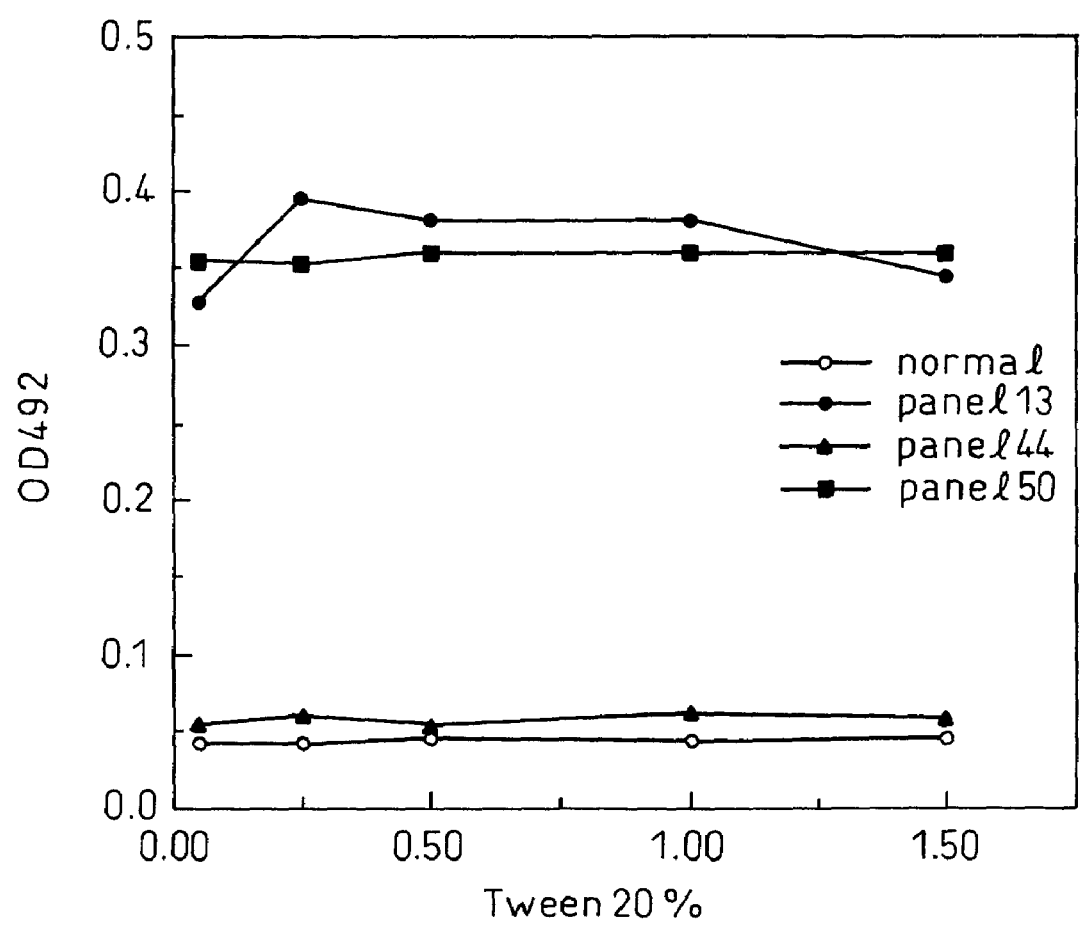
FIG. 12 is a graph showing the effect of concentration of added Tween 20 on sample treatment. Sera from normal healthy human subjects (normal) and HCV-RNA-positive panel sera 13 and 50 were used.

To 100 μl of a normal human serum and HCV-RNA-positive sera were added 100 μl of the treatment solution containing a different concentration of Triton X100 (6 M guanidine hydrochloride, 0.5 N HCl, 12.5% Triton X100). The mixtures were treated at room temperature for 30 minutes, and 80 μl each of the treated mixtures was used as a sample. The result obtained using the assay method described below is shown in FIG. 12 with the Tween 20 concentration at the time of treatment taken as the abscissa.

4) Reaction Temperature

Figure 13:
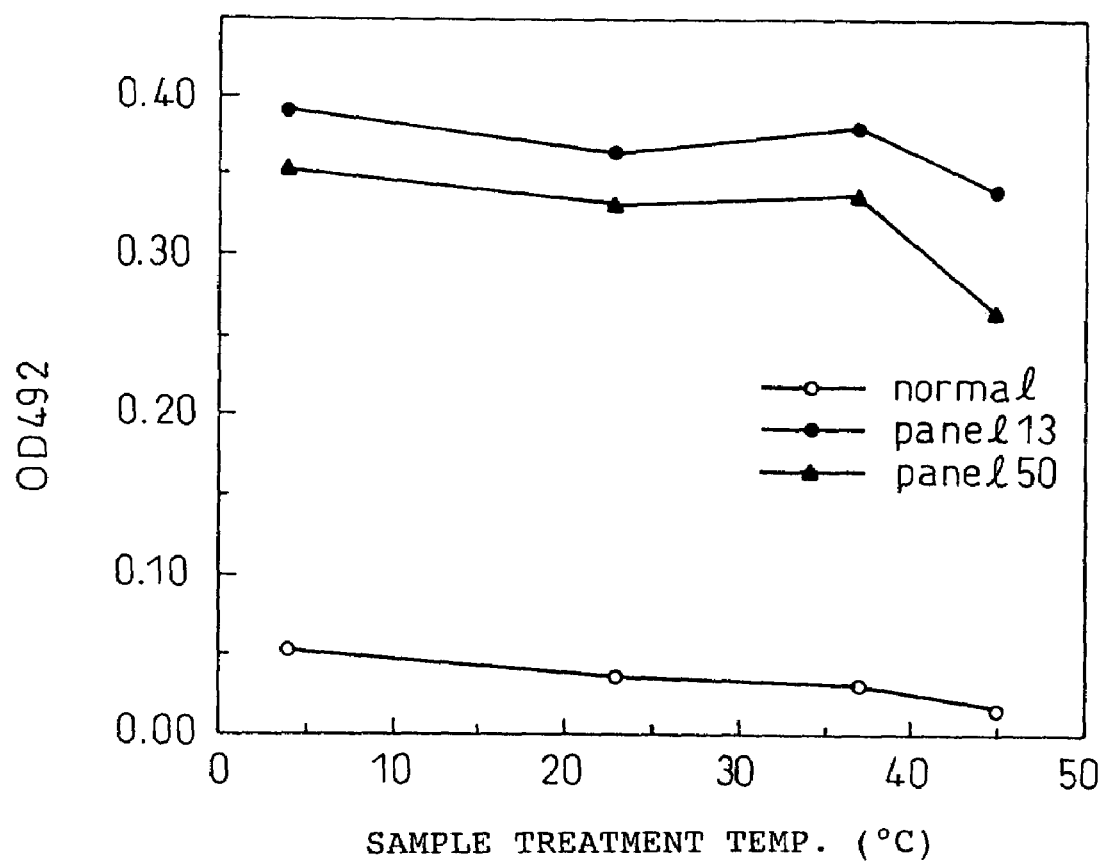
FIG. 13 is a graph showing the effect of temperature during sample treatment. Sera from normal healthy human subjects (normal) and HCV-RNA-positive panel sera 13 and 50 were used.

To 100 μl of a normal human serum and HCV-RNA-positive sera were added 100 μl of the treatment solution (6 M guanidine hydrochloride, 0.5 N HCl, 12.5% Triton X, 0.75% Tween 20). The mixtures were treated at 4° C., room temperature (23° C.), 37° C., and 45° C. for 30 minutes, and 80 μl each of the treated mixtures were used as a sample. The result obtained using the assay method described below is shown in FIG. 13.

Assay Methods

Samples obtained in the study on the condition of serum treatment were each evaluated using the respective assay method described below. Thus, an anti-HCV core antigen monoclonal antibody (a mixture of equal amounts of antibody C11-14 and C11-11) was diluted to a final total concentration of 6 μg/ml in 0.1 M carbonate buffer, pH 9.6, and 100 μl each of the dilutions was dispensed per well of a 96-well microtiter plate (manufactured by Nunc). After the plate was incubated overnight at 4° C., it was washed twice with 0.35 ml of 10 mM sodium phosphate buffer, pH 7.3, containing 0.15 M NaCl. Then, 0.35 ml of 10 mM sodium phosphate buffer, pH 7.35, containing 0.5% casein-Na (hereinafter referred to as the blocking solution) was added and the plate was further incubated at room temperature for 2 hours.

After the blocking solution was removed, 160 μl of the mixture of 140 μl of 100 mM sodium phosphate buffer, pH 7.3, containing 0.15 M NaCl, 1% BSA, 0.5% casein-Na, and 0.05% Tween 20, and 20 μl of 1 M Tris (hereinafter referred to as the reaction buffer), and samples for measurement obtained by the above-mentioned serum treating method were added into respective wells, incubated at room temperature for 2 hours, washed five times with 300 μl of the wash solution, and then 100 μl of the peroxidase (POD)-labeled monoclonal antibody (C11-10) was added and was incubated at room temperature for 30 minutes. After the incubation was over, the plate was washed five times with 300 μl of the above wash solution. One hundred microliters of the substrate (ortho-phenylene diamine, hereinafter referred to as OPD) solution was added to the plate and the plate was incubated at room temperature for 30 minutes, followed by the addition of 100 μl of 2 N sulfuric acid solution. Absorbance was measured at a wavelength of 492 nm (OD492) with the absorbance at 630 nm as a reference.

Each treatment condition was optimized as shown in FIGS. 10 to 13. It was difficult to detect the core antigen in the untreated samples, but such a simple treatment drastically enabled the detection of the core antigen. In any case no enhancement in signals was observed in the healthy humans. It was also shown that the core antigen can be satisfactorily detected by employing the condition of guanidine hydrochloride at 2 M or greater and Triton X100 at 0.2% or greater, and a temperature range of 4° C. to 45° C.

Example 11

The Detection and Assay Method of the Core Antigen

To 100 μl of serum was added 100 μl of a treatment solution (6 M guanidine hydrochloride, 0.5 N HCl, 12.5% Triton X100, 0.75% Tween 20). It was treated at room temperature for 30 minutes, and 100 μl of the treated mixture was used as a sample.

An anti-HCV core antigen monoclonal antibody (a mixture of equal amounts of C11-14 and C11-11) was diluted to a final total concentration of 6 μg/ml in 0.1 M carbonate buffer, pH 9.6, and 100 μl each of the diluted mixture was dispensed per well of a 96-well microtiter plate (manufactured by Nunc).

After the plate was incubated overnight at 4° C., it was washed twice with 0.35 ml of 10 nM sodium phosphate buffer, pH 7.3, containing 0.15 M NaCl. Then, 0.35 ml of the blocking solution was added and the plate was further allowed to stand at room temperature for 2 hours. After the blocking solution was removed, 150 μl of the reaction buffer and samples for measurement obtained in the above treating method were added into respective wells, and incubated at room temperature for 2 hours.

The plate was washed five times with 300 μl of the wash solution, and then 100 μl of a peroxidase (POD)-labeled monoclonal antibody (C11-10) was added to the plate. The plate was incubated at room temperature for 30 minutes. Then the plate was washed five times with 300 μl of the wash solution, and 100 μl of the substrate (OPD) solution was added. After incubating the plate at room temperature for 45 minutes, 100 μl of 2 N sulfuric acid solution was added. Absorbance was measured at a wavelength of 492 nm (OD492) with the absorbance at 630 nm as a reference. As a standard serum, the panel serum 50, defined as 1 U/ml, was serially diluted in 10 mM sodium phosphate buffer, pH 7.3, containing 1% BSA, which was similarly treated and measured.

Figure 14:
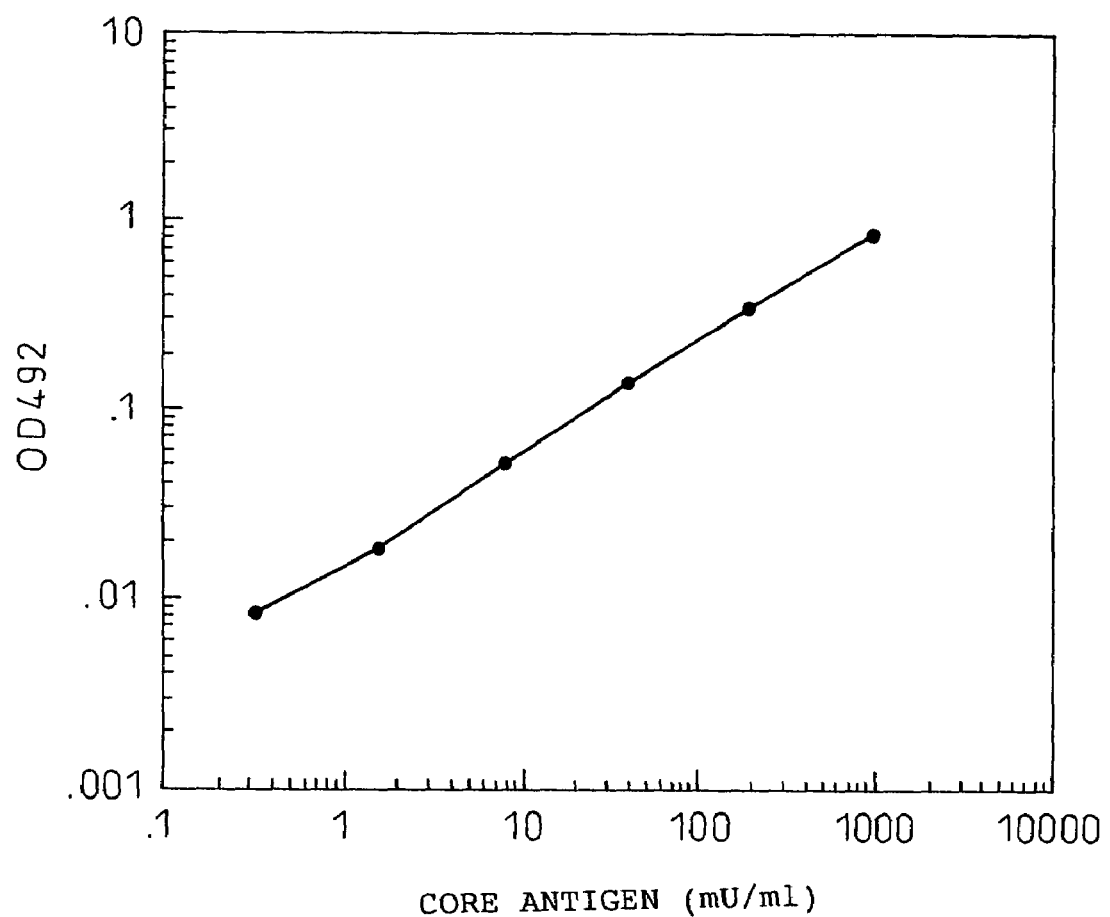
FIG. 14 is a graph showing the dilution standard curve and the detection limit of a sandwich immunoassay system in which a standard panel serum 50, defined as 1 U/ml, was serially diluted and subjected to a sample treating method, and then was measured.
Figure 15:
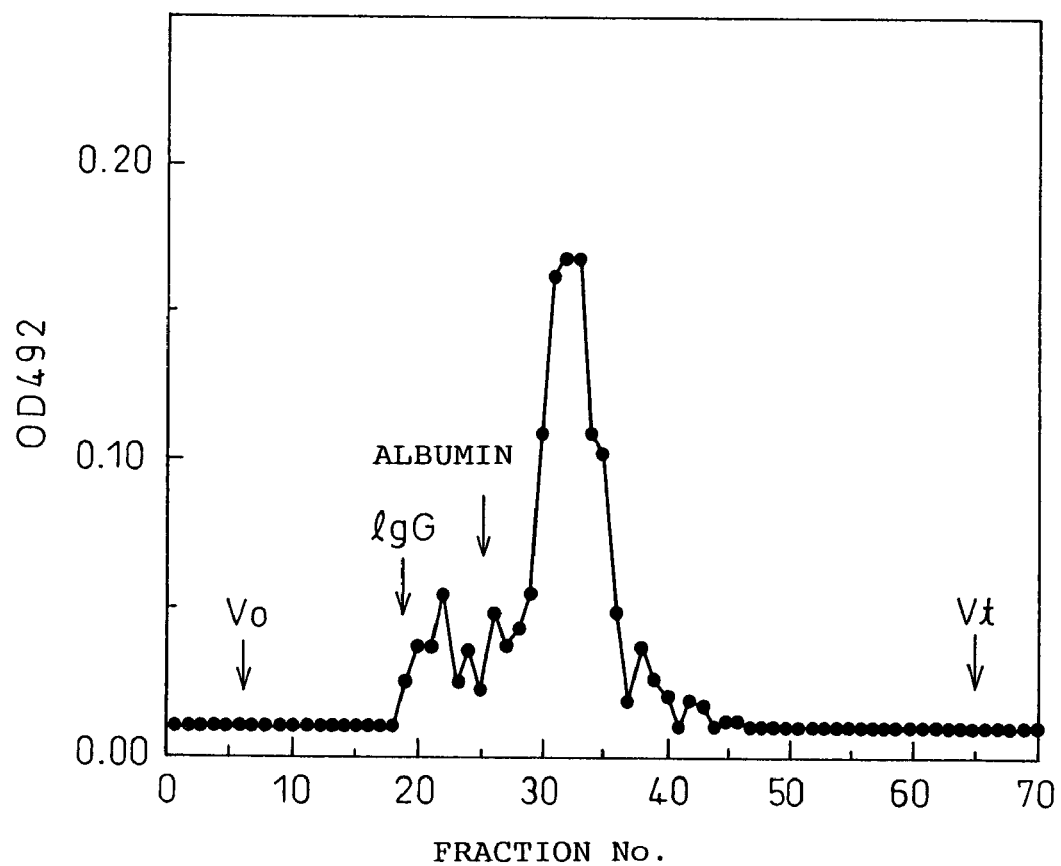
FIG. 15 shows an immunological activity of core antigen in fractions obtained by fractionation with a gel filtration column of the panel serum 13 that was subjected to sample treating method. The molecular weight is about 150 kD and about 68 kD for IgG and albumin, respectively.

FIG. 14 shows a dilution line of the panel serum 50 used as a standard serum. The core antigen in the sample was determined in a dose-dependent manner and could be detected to a level as low as about 0.5 mU/ml. It was demonstrated, therefore, that by combining a very simple method of sample treatment and the monoclonal antibody of the present invention, the HCV core antigen can be detected or quantitated.

Example 12

Analysis the Molecular Form Recognized in the Serum Treatment and in the Assay Method Each method of serum treatment was used to treat 0.25 ml of the panel serum 13. The treated serum was fractionated by a gel filtration column (Superdex 200HR, 1×30), and anti-core immunological activity in the fractions was measured. The result is shown in Table 15. The figure suggested that molecules having a molecular weight of about 20 to 30 kDa are being recognized and that the core antigen in the virus has been released from various interactions through the disruption of the virus and the inactivation of the anti-core antibody in the serum by the above-mentioned pretreatment.

Example 13

Assay Method of the Core Antigen in the Serum

Sera determined to have $10^3$ to $10^7$ copies/ml of HCV-RNA using AmpliCore HCV Monitor kit (Roche), a PCR method, and normal human sera were used to quantitate the HCV core antigen in the sera using the method described above.

Figure 16:
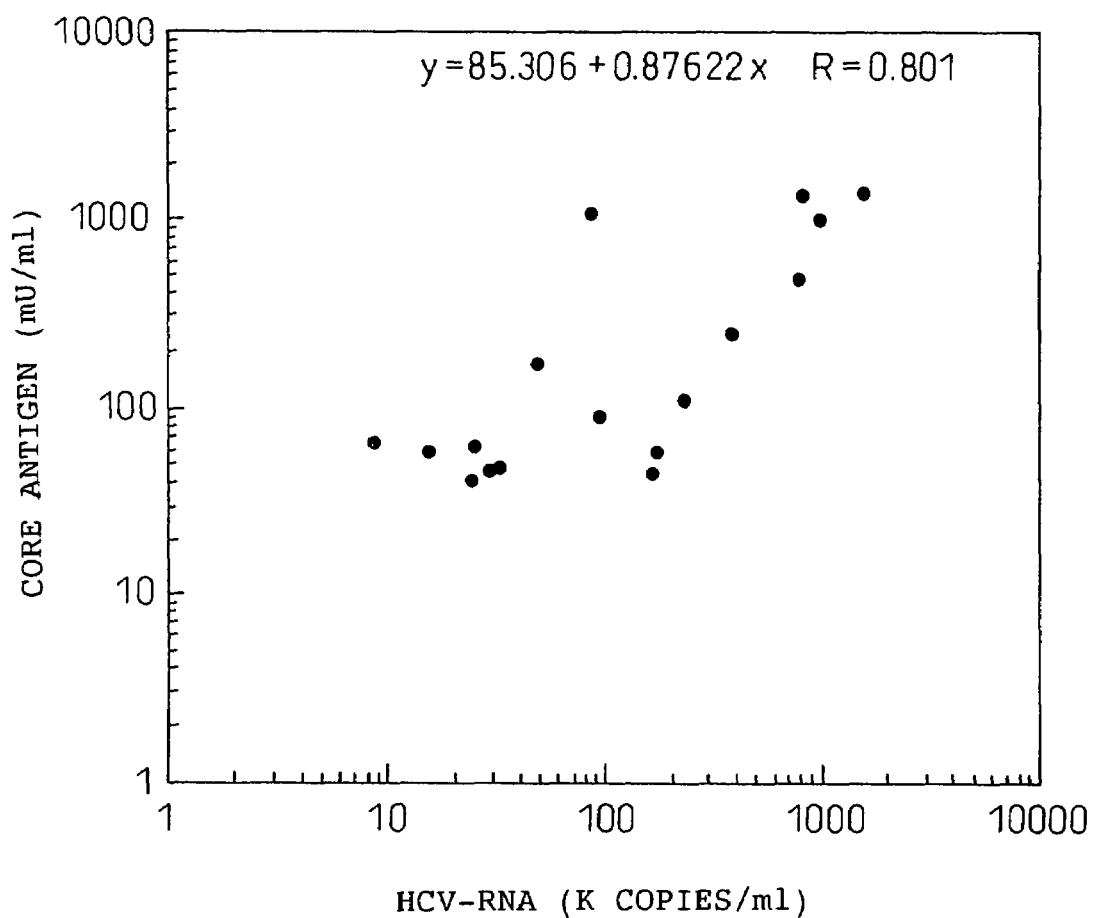
FIG. 16 is a graph showing a correlation between the activity of core antigen released and the amount of HCV-RNA determined using Amplicore HCV Monitor (PCR method) of a sample which was subjected to a sample treating method of the present invention and which tested positive by Amplicore HCV Monitor (PCR method).

As a standard serum the panel serum 50 (sefined as 1 U/ml) was serially diluted in 10 mM sodium phosphate buffer, pH 7.3, containing 1% BSA, and treated in a similar manner. The result is shown in Table 8. Of the samples tested, the core antigen in all the normal human sera was below the detection limit and could be detected in all of the PCR-positive samples. The correlation is shown in FIG. 16, which revealed that the correlation with the PCR method was also as high as 0.8 or greater.

TABLE 8

Levels of HCV-RNA and the core antigen

| Sample # | | RNA (K copies/ml) | Core antigen (mU/ml) |
|---|---|---|---|
| Normal human serum | 1 | — | N.D. |
| | 2 | — | N.D. |
| | 3 | — | N.D. |
| | 4 | — | N.D. |
| | 5 | — | N.D. |
| | 6 | — | N.D. |
| | 7 | — | N.D. |
| Panel serum | 1 | 50 | 166.4 |
| | 7 | 830 | 471.1 |
| | 8 | 26 | 61.5 |
| | 11 | 240 | 107.4 |
| | 13 | 1600 | 1426 |
| | 15 | 25 | 40.1 |
| | 16 | 400 | 240.3 |
| | 19 | 840 | 1369 |
| | 26 | 87 | 1093 |
| | 31 | 30 | 45.8 |
| | 33 | 16 | 58.5 |
| | 39 | 97 | 89.0 |
| | 41 | 170 | 43.9 |
| | 44 | 180 | 57.5 |
| | 49 | 33 | 47.7 |
| | 50 | 1000 | 1005 |
| | 84 | 8.7 | 63.5 |

N.D.: Not detected

Example 14

Detection of the Hepatitis B Virus (HBV) Core Antigen

We have so far explained the detection of the HCV core antigen. We have investigated whether this treating method is applicable to the detection of structural proteins in other viruses.

A monoclonal antibody (Tokushu Menneki Kenkyuusho [Special Immunology Research Institute]) against HBV core antigen was diluted to a concentration of 3 μg/ml in 0.1 M carbonate buffer, pH 9.6, and was dispensed in an aliquot of 100 μl. After incubating overnight at 4° C., the plate was washed with a phosphate buffer, and a 350 μl aliquot of 1% BSA solution was dispensed to the plate. After allowing to stand at room temperature for 2 hours, the 1% BSA solution was aspirated off, and 200 μl of the reaction solution was added.

A recombinant HBV core antigen was used as a standard, and five patient sera that tested positive for HBe antigen and negative for anti-HBe antibody and ten normal human sera were used as samples. To 100 μl of a sample, 50 μl of a treatment reagent (7.5% SDS, 0.75% CHAPS, 0.15% Triton X100, 2 M urea, 0.1 M histidine, 0.1 M tryptophan) was added and treated at 56° C. for 30 minutes. After the treatment, 50 μl thereof was added to a well filled with the reaction solution, and was incubated at room temperature for 90 minutes.

As a comparison (without pretreatment), 100 μl of each sample was diluted with 50 μl of purified water and 50 μl of the diluted sample was used for the reaction. After washing five times with the wash solution, a biotin-labeled anti-HBV core monoclonal antibody (a mixture of equal amounts of HBc-2, HBc-5, HBc-14) was added, and incubated at room temperature for 30 minutes. After washing five times with the wash solution, the avidin-labeled alkaline phosphatase was added and the mixture was reacted at room temperature for 30 minutes.

Figure 17:
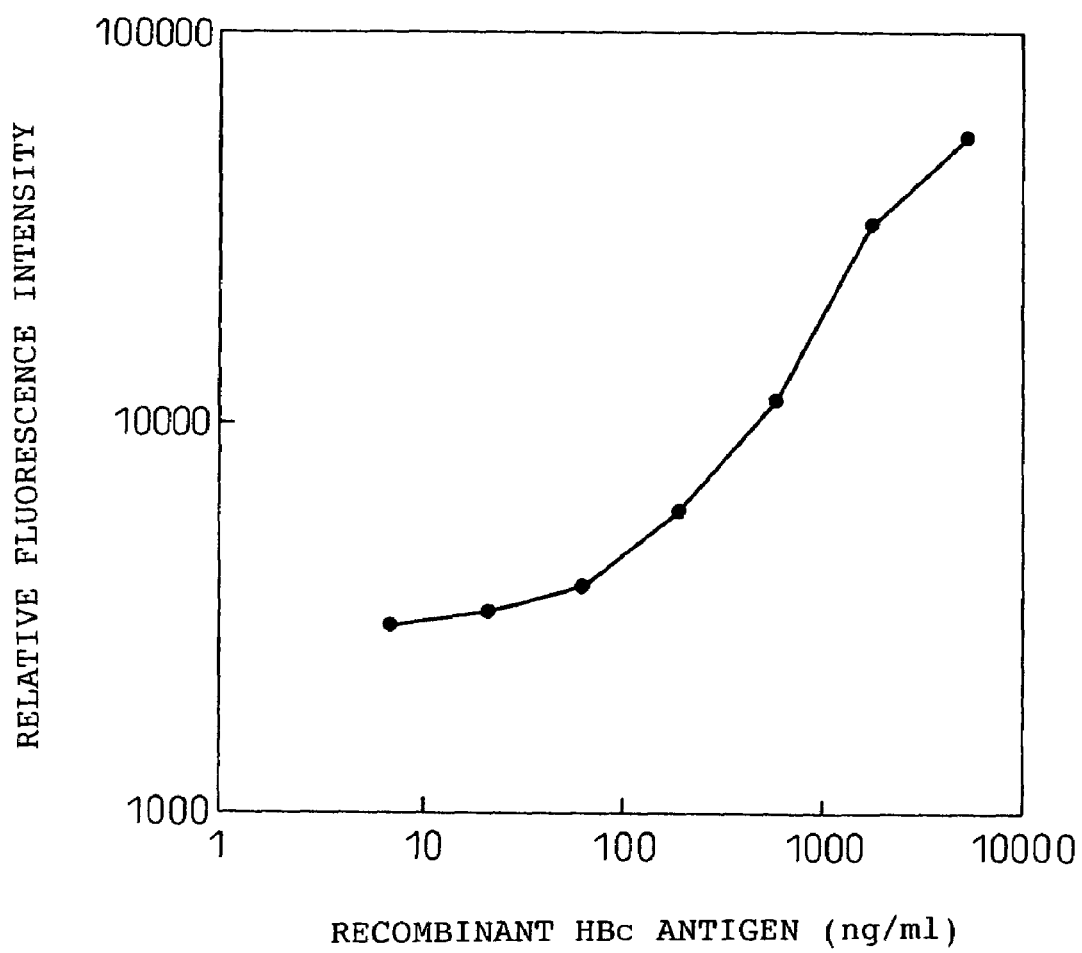
FIG. 17 shows a standard curve obtained by determination of recombinant hepatitis B virus (HBV) core antigen according to the present invention.

After washing five times with the wash solution, CDPstar (Emerald II as the sensitizer) was added, reacted at room temperature for 15 minutes, and relative chemiluminescence thereof was measured. A standard curve for a serially diluted recombinant HBV core antigen is shown in FIG. 17, and the amount of the core antigen in the measured samples is shown in Table 9. The detection limit was 21 ng/ml. When a cut-off value that distinguishes the core antigen-positive from the negative was defined at 60 ng/ml, all 10 normal human sera, with or without pretreatment, tested negative for the core antigen, and in the sera of patients with hepatitis B virus, the core antigen could not be detected in the case of no pretreatment, but with pretreatment, all the sera tested positive for the core antigen.

It is thought that in the sera of patients with the hepatitis B virus, pretreatment disrupted the virus particle and inactivated the anti-HBc antibody, thereby enabling the detection of the core antigen. From the foregoing, it was confirmed that this method of sample treatment is useful for the detection of the structural proteins of viruses other than HCV, such as HBV, that have DNA as the genome. Needless to say, this holds true for HCV-related viruses such as flaviviruses and retroviruses, for example HIV.

TABLE 9

| Sample # | | non-treated | | pre-treated | |
|---|---|---|---|---|---|
| | | HBV core Ag (ng/ml) | Judged | HBV core Ag (ng/ml) | Judged |
| Normal human sample | 1 | <21 | Neg. | <21 | Neg. |
| | 2 | <21 | Neg. | <21 | Neg. |
| | 3 | <21 | Neg. | <21 | Neg. |
| | 4 | <21 | Neg. | <21 | Neg. |
| | 5 | <21 | Neg. | 46 | Neg. |
| | 6 | <21 | Neg. | <21 | Neg. |
| | 7 | <21 | Neg. | 47 | Neg. |
| | 8 | <21 | Neg. | <21 | Neg. |
| | 9 | <21 | Neg. | 26 | Neg. |
| | 10 | <21 | Neg. | 56 | Neg. |
| HBV sample | 11 | <21 | Neg. | 98 | Pos. |
| | 15 | <21 | Neg. | 94 | Pos. |
| | 20 | <21 | Neg. | 780 | Pos. |
| | 21 | <21 | Neg. | 270 | Pos. |
| | 46 | <21 | Neg. | 630 | Pos. |

Example 15

Method for Effective Detection without Pretreatment of the Antigen

HCV particle-containing samples were diluted in a surfactant-added reaction solution, and the efficiency of detecting the HCV antigen was investigated.

The detection of the HCV core antigen was carried out by a sandwich enzymeimmunoassay (EIA) using monoclonal antibody against the HCV core antigen. Among the monoclonal antibodies obtained in Example 3, C11-3 and C11-7 were used as the antibody for capturing the core antigen and C11-10 and C11-14 were used as the antibody for detecting the captured core antigen.

EIA was essentially carried out using the following conditions. Solutions of monoclonal antibodies C11-3 and C11-7, each of which was diluted to 4 μg/ml in an acetate buffer, were added to a microtiter plate and were incubated overnight at 4° C. After washing with the phosphate buffer, a phosphate buffer containing 1% BSA, was added to effect blocking. To the plate were added 100 μl of the reaction solution and 100 μl of the sample. The plate was then stirred and incubated at room temperature for 1.5 hour. Unreacted substances were removed by washing with the phosphate buffer to which a low concentration of a surfactant had been added. Then the alkaline phosphatase-labeled monoclonal antibodies C11-10 and C11-14 were added and reacted at room temperature for 30 minutes. After the reaction is over, unreacted substances were removed by washing with the phosphate buffer to which a low concentration of a surfactant had been added. Then a substrate solution (CDP-Star/Emerald11) was added and reacted at room temperature for 20 minutes. The amount of luminescence was measured.

To the above reaction, various surfactants were added to investigate their effects. By using HCV-positive sera in which the titer of antibody to HCV is below the detection limit and virtually no antibody to HCV is contained, the activity of the core antigen based on the amount of luminescence was expressed in terms of a reaction ratio relative to the amount of luminescence of the normal human serum that was defined as 1.0. The results are shown in Tables 10 and 11.

TABLE 10

Reactivity relative to normal human serum (S/N ratio)

| | HLB | (%) | NO 45 | NO 46 | NO 3 | NO 7 | NO 19 |
|---|---|---|---|---|---|---|---|
| No addition | | | 15.67 | 1.00 | 1.15 | 1.34 | 1.19 |
| Judgement criteria | | | >30.0 | >2.0 | >2.0 | >2.0 | >2.0 |
| Additive | | | | | | | |
| Anionic surfactant | | | | | | | |
| sodium dodecyl sulfate | 40.0 | 0.5 | 5.42 | | | | |
| | | 2.0 | 5.73 | | | | |
| sodium dodecyl-N-sarcosinate | | 0.5 | 12.79 | 2.70 | | | |
| | | 2.0 | 125.43 | 7.27 | 3.83 | 3.70 | 6.71 |
| perfluoroalkyl-carboxylic acid S-113 | | 0.5 | 10.55 | 1.27 | | | |
| | | 2.0 | 6.72 | 0.91 | | | |
| Cationic surfactant | | | | | | | |
| cetyltrimethyl-ammonium bromide | | 0.5 | 72.97 | 7.42 | 3.09 | 3.52 | 5.43 |
| | | 2.0 | 44.55 | 5.35 | | | |
| dodecylpyridinium chloride | | 0.5 | 53.43 | 4.70 | 2.05 | 1.52 | 2.33 |
| | | 2.0 | 12.44 | 2.49 | | | |
| n-dodecyltrimethyl-ammonium | | 0.5 | 66.84 | 4.43 | 2.41 | 1.63 | 2.67 |
| | | 2.0 | 27.98 | 3.77 | | | |
| tetradecyl-ammonium bromide | | 0.05 | 14.69 | | | | |
| n-octyltrimethyl-ammonium chloride | | 0.5 | 12.57 | | 1.00 | 0.74 | 0.99 |
| | | 2.0 | 11.46 | | | | |
| n-decyltrimethyl-ammonium chloride | | 0.5 | 17.50 | | 0.88 | 0.80 | 0.72 |
| | | 2.0 | 45.21 | | 1.12 | 1.08 | 1.41 |
| Amphoteric surfactant | | | | | | | |
| CHAPS | | 0.5 | 29.57 | | | | |
| | | 2.0 | 25.32 | | 1.63 | 1.82 | 2.42 |
| perfluoroalkyl-betaine S-132 (from ASAHI GLASS) | | 0.5 | 11.07 | 1.61 | | | |
| | | 2.0 | 10.77 | 1.49 | | | |
| 3-(dodecyldimethyl-ammonio)-1-propane-sulfonic acid | | 0.5 | 57.69 | | | | |
| | | 2.0 | 113.19 | | 4.57 | 3.44 | 5.26 |

TABLE 11

Reactivity relative to normal human serum (S/N ratio)

| | HLB | (%) | NO 45 | NO 46 | NO 3 | NO 7 | NO 19 |
|---|---|---|---|---|---|---|---|
| No addition | | | 15.67 | 1.00 | 1.15 | 1.34 | 1.19 |
| Judgement criteria | | | >30.0 | >2.0 | >2.0 | >2.0 | >2.0 |
| Additive | | | | | | | |
| nonionic surfactant | | | | | | | |
| MEGA-10 | | 0.5 | 32.11 | 3.38 | | | |
| | | 2.0 | 38.49 | 3.53 | 1.97 | 1.87 | 2.84 |
| Tween 20 | 16.7 | 0.5 | 16.88 | | | | |
| | | 2.0 | 12.36 | | | | |
| Tween 40 | 15.6 | 0.5 | 14.96 | | 1.02 | 0.99 | 1.41 |
| | | 2.0 | 19.10 | | 1.32 | 1.25 | 1.64 |
| Tween 80 | 15.0 | 0.5 | 12.45 | | 1.33 | 1.23 | 1.10 |
| | | 2.0 | 17.47 | | | | |
| Nonidet P-40 | 13.1 | 0.5 | 43.14 | | 3.09 | 2.95 | 4.58 |
| octyl glucoside | | 0.5 | 12.48 | | 0.90 | 0.60 | 0.97 |
| | | 2.0 | 25.07 | | 1.92 | 1.20 | 2.63 |
| Triton N101 | 13.4 | 0.5 | 26.50 | | 1.85 | 1.62 | 2.70 |
| | | 2.0 | 60.84 | | 2.23 | 2.28 | 3.81 |
| Triton X100 | 13.5 | 0.5 | 27.72 | | | | |
| | | 2.0 | 71.08 | | 2.90 | 2.34 | 3.86 |
| Triton X114 | 12.4 | 0.5 | 31.49 | | 2.04 | 1.65 | 2.77 |
| | | 2.0 | 58.62 | | 1.92 | 2.11 | 2.51 |
| Triton X305 | 17.3 | 0.5 | 10.50 | | 0.94 | 0.97 | 1.08 |
| | | 2.0 | 25.91 | | 1.30 | 1.24 | 1.87 |
| Triton X405 | 17.9 | 0.5 | 12.54 | | 0.86 | 0.78 | 1.04 |
| | | 2.0 | 24.92 | | 1.21 | 1.24 | 1.25 |
| Others | | | | | | | |
| benzyldimethyl- | | 0.5 | 5.45 | 1.00 | | | |
| ammonium chloride | | 2.0 | 7.01 | 1.12 | | | |
| triethylamine | | 0.5 | 3.89 | 0.97 | | | |
| Surfactant mixture | | | | | | | |
| 2% sodium dodecyl-N-sarcosinate + 2% Triton X100 | | | 244.13 | | 6.11 | 5.50 | 12.71 |

The results revealed that the addition of a nonionic surfactant having an HLB of 12 to 14, as represented by Triton X100, causes an increase in the amount of luminescence thereby enhancing detection sensitivity in HCV-positive sera compared to the normal human sera. It was also clarified that, similarly, as represented by sodium dodecyl-N-sarcosinate and dodecyl trimethylammonium, the addition of a surfactant having in its structure a straight-chain alkyl group having at the same time 10 or more carbon atoms and a secondary, tertiary, or quaternary amine causes an increase in detection sensitivity in HCV-positive sera. No such increase in sensitivity was observed with the above surfactant with an alkyl group having not more than 8 carbons (n-octyl trimethylammonium chloride). It was also found that by mixing and adding these two surfactants (in Table 11, 2% sodium dodecyl-N-sarcosinate and 2% Triton X100 were mixed), detection sensitivity in HCV-positive sera can be further enhanced.

Example 16

Detection of the Core Antigen in the Samples During a Period Between after HCV Infection and Before the Appearance of Anti-HCV Antibody (Window Period)

By adding 2% Triton X100 and 2% sodium dodecyl-N-sarcosinate to the primary reaction solution, a commercially available seroconversion panel PHV905 (B.B.I. inc.) was measured according to Example 15. The PHV905 panel used turned positive on day 21 after the start of observation (serum No. PHV905-7) when measured by the anti-HCV antibody test (Ortho EIA 3.0). In the test, the antibody titer is expressed in a cut-off index (S/CO) with a value of 1.0 or greater being judged as positive. The activity of the HCV core antigen (the amount of luminescence) was expressed in the reactivity (S/N) relative to that of the normal human serum that was defined as 1.0.

As shown in FIG. 12, the activity of the core antigen is observed before the anti-HCV antibody appears, the addition of a surfactant exposed the core antigen from the virus particle, which reacted with the immobilized monoclonal antibody, thereby confirming the detection of the core antigen.

TABLE 12

| Serum No. | Days after start of observation | HCV core Ag activity (S/N) | Anti-HCV Ab titer (S/CO) |
|---|---|---|---|
| PHV905-1 | 0 | 5.32 | 0.000 |
| 905-2 | 4 | 8.30 | 0.000 |
| 905-3 | 7 | 15.63 | 0.000 |
| 905-4 | 11 | 4.37 | 0.300 |
| 905-5 | 14 | 14.75 | 0.700 |
| 905-6 | 18 | 7.57 | 0.700 |
| 905-7 | 21 | 4.82 | 2.500 |
| 905-8 | 25 | 3.31 | 5.000 |
| 905-9 | 28 | 1.61 | 5.000 |

Reference to microorganisms defined in rule 13-2 of the Rule based on Patent Cooperation Treaty Name of depository: the National Institute of Bioscience and Human Technology, Agency of Industrial Science and Technology Address of depolsitory: 1-3, Higashi 1-chome, Tsukuba city, Ibalaki pref., Japan (Zip code 305)

(1) Indication of microorganism: HC11-3

Date deposited: Jul. 4, 1997
Deposit number: FERM BP-6002

(2) Indication of microorganism: HC11-7

Date deposited: Jul. 4, 1997
Deposit number: FERM BP-6003

(3) Indication of microorganism: HC11-10

Date deposited: Jul. 4, 1997
Deposit number: FERM BP-6004

(4) Indication of microorganism: HC11-11

Date deposited: Jul. 4, 1997
Deposit number: FERM BP-6005

(5) Indication of microorganism: HC11-14

Date deposited: Jul. 4, 1997
Deposit number: FERM BP-6006

The invention claimed is:

1. A method for detecting a hepatitis C virus (HCV) in a sample by obtaining a sample suitable for detection of virus by a probe monoclonal antibody, comprising the steps of:
   (1) treating a virus-containing sample with a treatment solution containing (a) an anionic surfactant and (b) at least one agent selected from the group consisting of an amphoteric surfactant, a nonionic surfactant and a protein denaturant; such that the virus particle is disrupted, the virus antigen is exposed or released such that the virus antigen is denatured; and antibodies against the virus antigen, if present in the sample, are inactivated; and
   (2) adding the treated sample to a probe monoclonal antibody that has been immobilized to a solid support, wherein the concentration of the surfactants used during the treatment step are diluted to an extent that said surfactants exhibit little or no denaturing properties to the probe monoclonal antibody, adding a reaction buffer to said treatment sample and probe monoclonal antibody and detecting the denatured virus antigen by immunoassay using the probe monoclonal antibody.

2. The method according to claim 1, wherein said treatment solution further contains urea, an imidazole ring-containing compound or an indole ring-containing compound.

3. The method according to claim 1, wherein said treatment solution further contains urea.

4. A method according to claim 1, wherein the at least one agent consists of the amphoteric surfactant and one agent selected from either the nonionic surfactant or the protein denaturant, and wherein the denaturing effect of the anionic surfactant to the probe monoclonal antibody is reduced by the amphoteric surfactant and the one agent selected from the nonionic surfactant or the protein denaturant.

5. The method according to claim 4, wherein said treatment solution further contains urea.

6. The method according to claim 1, wherein the at least one agent consists of the amphoteric surfactant, the nonionic surfactant and the protein denaturant, and wherein the denaturing effect of the anionic surfactant to the probe monoclonal antibody is reduced by the amphoteric surfactant, the nonionic surfactant, and the protein denaturant.

7. A method for detecting a hepatitis B virus (HBV) in a sample by obtaining a sample suitable for detection of virus by a probe monoclonal antibody, comprising the steps of:
   (1) treating a virus-containing sample with a treatment solution containing (a) an anionic surfactant and (b) at least one agent selected from the group consisting of an amphoteric surfactant, a nonionic surfactant and a protein denaturant; such that the virus particle is disrupted, the virus antigen is exposed or released such that the virus antigen is denatured; and antibodies against the virus antigen, if present in the sample, are inactivated; and
   (2) adding the treated sample to a probe monoclonal antibody that has been immobilized to a solid support, wherein the concentration of the surfactants used during the treatment step are diluted to an extent that said surfactants exhibit little or no denaturing properties to the probe monoclonal antibody, adding a reaction buffer to said treatment sample and probe monoclonal antibody and detecting the denatured virus antigen by immunoassay using the probe monoclonal antibody.

8. The method according to claim 7, wherein said treatment solution further contains urea, an imidazole ring-containing compound or an indole ring-containing compound.

9. The method according to claim 7, wherein said treatment solution further contains urea.

10. The method according to claim 7, wherein the at least one agent consists of the amphoteric surfactant and one agent selected from either the nonionic surfactant or the protein denaturant, and wherein the denaturing effect of the anionic surfactant to the probe monoclonal antibody is reduced by the amphoteric surfactant and the one agent selected from either the nonionic surfactant or the protein denaturant.

11. The method according to claim 10, wherein said treatment solution further contains urea.

12. The method according to claim 7, wherein the at least one agent consists of the amphoteric surfactant, the nonionic surfactant and the protein denaturant, and wherein the denaturing effect of the anionic surfactant to the probe monoclonal antibody is reduced by the amphoteric surfactant, the nonionic surfactant, and the protein denaturant.

* * * * *

SEQUENCE LISTING

<160> NUMBER OF SEQ ID NOS: 8

<210> SEQ ID NO 1
<211> LENGTH: 177
<212> TYPE: PRT
<213> ORGANISM: Hepatitis C virus

<400> SEQUENCE: 1

Met Lys Ala Ile Phe Val Leu Lys Gly Ser Leu Asp Arg Asp Pro Glu
1               5                   10                  15

Phe Met Gly Thr Asn Pro Lys Pro Gln Arg Lys Thr Lys Arg Asn Thr
            20                  25                  30

Asn Arg Arg Pro Gln Asp Val Lys Phe Pro Gly Gly Gly Gln Ile Val
        35                  40                  45

Gly Gly Val Tyr Leu Leu Pro Arg Arg Gly Pro Arg Leu Gly Val Arg
    50                  55                  60

Ala Thr Arg Lys Thr Ser Lys Arg Ser Gln Pro Arg Gly Gly Arg Arg
65                  70                  75                  80

Pro Ile Pro Lys Asp Arg Arg Ser Thr Gly Lys Ser Trp Gly Lys Pro
                85                  90                  95

Gly Tyr Pro Trp Pro Leu Tyr Gly Asn Glu Gly Leu Gly Trp Ala Gly
            100                 105                 110

Trp Leu Leu Ser Pro Arg Gly Ser Arg Pro Ser Trp Gly Pro Thr Asp
        115                 120                 125

Pro Arg His Arg Ser Arg Asn Val Gly Lys Val Ile Asp Thr Leu Thr
    130                 135                 140

Cys Gly Phe Ala Asp Leu Met Gly Tyr Ile Phe Arg Val Gly Ala Phe
145                 150                 155                 160

Leu Gly Gly Ala Ala Arg Ala Leu Ala His Gly Val Arg Val Leu Glu
                165                 170                 175

Asp

<210> SEQ ID NO 2
<211> LENGTH: 160
<212> TYPE: PRT
<213> ORGANISM: Hepatitis C virus

<400> SEQUENCE: 2

Met Gly Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Lys Arg Ser Gln Pro Arg Gly Gly Arg Arg Pro
    50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg His Arg Ser Arg Asn Val Gly Lys Val Ile Asp Thr Leu Thr Cys
        115                 120                 125

-continued

```
Gly Phe Ala Asp Leu Met Gly Tyr Ile Phe Arg Val Gly Ala Phe Leu
            130                 135                 140

Gly Gly Ala Ala Arg Ala Leu Ala His Gly Val Arg Val Leu Glu Asp
145                 150                 155                 160

<210> SEQ ID NO 3
<211> LENGTH: 20
<212> TYPE: PRT
<213> ORGANISM: Artificial Sequence
<220> FEATURE:
<223> OTHER INFORMATION: Recognition site of Antibody C11-10

<400> SEQUENCE: 3

Asp Val Lys Phe Pro Gly Gly Gly Gln Ile Val Gly Gly Val Tyr Leu
1               5                   10                  15

Leu Pro Arg Arg
            20

<210> SEQ ID NO 4
<211> LENGTH: 10
<212> TYPE: PRT
<213> ORGANISM: Artificial Sequence
<220> FEATURE:
<223> OTHER INFORMATION: Recognition site of Antibody C11-14

<400> SEQUENCE: 4

Gly Pro Arg Leu Gly Val Arg Ala Thr Arg
1               5                   10

<210> SEQ ID NO 5
<211> LENGTH: 21
<212> TYPE: PRT
<213> ORGANISM: Artificial Sequence
<220> FEATURE:
<223> OTHER INFORMATION: Recognition site of Antibody C11-3

<400> SEQUENCE: 5

Pro Arg Gly Ser Arg Pro Ser Trp Gly Pro Thr Asp Pro Arg His Arg
1               5                   10                  15

Ser Arg Asn Val Gly
            20

<210> SEQ ID NO 6
<211> LENGTH: 20
<212> TYPE: PRT
<213> ORGANISM: Artificial Sequence
<220> FEATURE:
<223> OTHER INFORMATION: Recognition site of Antibody c11-7

<400> SEQUENCE: 6

Asp Pro Arg His Arg Ser Arg Asn Val Gly Lys Val Ile Asp Thr Leu
1               5                   10                  15

Thr Cys Gly Phe
            20

<210> SEQ ID NO 7
<211> LENGTH: 24
<212> TYPE: DNA
<213> ORGANISM: Artificial Sequence
<220> FEATURE:
<223> OTHER INFORMATION: synthetic DNA, PCR primer

<400> SEQUENCE: 7
gaattcatgg gcacgaatcc taaa                                          24
```

```
<210> SEQ ID NO 8
<211> LENGTH: 21
<212> TYPE: DNA
<213> ORGANISM: Artificial Sequence
<220> FEATURE:
<223> OTHER INFORMATION: Synthetic DNA, PCR primer

<400> SEQUENCE: 8
ttagtcctcc agaacccgga c                                              21
```